US012802216B2

(12) United States Patent
Fujimoto

(10) Patent No.: US 12,802,216 B2
(45) Date of Patent: Nov. 17, 2026

(54) DETERMINING MATERIAL COMPONENT CONCENTRATIONS IN A SAMPLE

(71) Applicant: ARKRAY, Inc., Kyoto (JP)

(72) Inventor: Koji Fujimoto, Kyoto (JP)

(73) Assignee: ARKRAY, INC., Kyoto (JP)

( * ) Notice: Subject to any disclaimer, the term of this patent is extended or adjusted under 35 U.S.C. 154(b) by 355 days.

(21) Appl. No.: 18/667,453

(22) Filed: May 17, 2024

(65) Prior Publication Data

US 2024/0385100 A1 Nov. 21, 2024

(30) Foreign Application Priority Data

May 17, 2023 (JP) ................................ 2023-081856
May 17, 2023 (JP) ................................ 2023-081902

(51) Int. Cl.
*G06T 7/00* (2017.01)
*G01N 15/075* (2024.01)
(Continued)

(52) U.S. Cl.
CPC ......... *G06T 7/0012* (2013.01); *G01N 15/075* (2024.01); *G01N 15/1433* (2024.01);
(Continued)

(58) Field of Classification Search
CPC ......... G06T 7/0012; G06T 2207/10056; G06T 2207/20081; G06T 2207/20084;
(Continued)

(56) References Cited

U.S. PATENT DOCUMENTS 5,911,002 A * 6/1999 Mitsuyama .......... G01N 33/493
382/156
2007/0027648 A1 2/2007 Kowata
(Continued)

FOREIGN PATENT DOCUMENTS

EP 693679 A1 * 1/1996
JP 2000-258335 A 9/2000
(Continued)

*Primary Examiner* — Francis C Gray
(74) *Attorney, Agent, or Firm* — Young Basile Hanlon & MacFarlane, P.C.

(57) ABSTRACT

An imaging device images a sample including material components. An acquisition unit acquires material component images from at least some sample images. A classification unit classifies the material component images into respective groups corresponding to respective types of material components. A transmission unit transmits at least one material component image to a remote processing device is configured to reclassify the images and return reclassification information for the images. An output unit outputs a first status, a second status, and/or a third status for a respective material component image. The first status indicates that the image has been classified but is waiting for an instruction to transmit the image to the remote processing device, the second status indicates that the reclassification information for the image from the remote processing device is pending, and the third status indicates that the reclassification information for the image is received from the remote processing device.

17 Claims, 21 Drawing Sheets

(51) Int. Cl.

| | |
|---|---|
| ***G01N 15/1433*** | (2024.01) |
| ***G01N 15/1434*** | (2024.01) |
| ***G01N 33/493*** | (2006.01) |
| ***G06V 10/94*** | (2022.01) |
| ***G06V 20/69*** | (2022.01) |
| *G01N 15/10* | (2006.01) |

(52) U.S. Cl.

CPC ....... *G01N 15/1436* (2013.01); *G01N 33/493* (2013.01); *G06V 10/94* (2022.01); *G06V 20/695* (2022.01); *G06V 20/698* (2022.01); *G01N 2015/1006* (2013.01); *G06T 2207/10056* (2013.01); *G06T 2207/20081* (2013.01); *G06T 2207/20084* (2013.01); *G06T 2207/20092* (2013.01); *G06T 2207/30004* (2013.01)

(58) Field of Classification Search

CPC .......... G06T 2207/20092; G06T 2207/30004; G01N 15/075; G01N 15/1433; G01N 15/1436; G01N 33/493; G01N 2015/1006; G01N 2015/1493; G01N 15/04; G01N 15/147; G01N 2015/1497; G06V 10/94; G06V 20/695; G06V 20/698

See application file for complete search history.

(56) References Cited

U.S. PATENT DOCUMENTS

| | | | | |
|---|---|---|---|---|
| 2007/0038406 | A1 | 2/2007 | Uemura et al. | |
| 2010/0169811 | A1* | 7/2010 | Yamada | G01N 15/1433 715/764 |
| 2011/0208536 | A1 | 8/2011 | Luscombe et al. | |
| 2012/0134559 | A1* | 5/2012 | Suzuki | G01N 15/1404 382/128 |
| 2013/0316444 | A1* | 11/2013 | Tanaka | G01N 15/1459 435/288.7 |
| 2014/0024072 | A1* | 1/2014 | Mizumoto | G01N 35/00603 422/68.1 |
| 2014/0273068 | A1* | 9/2014 | Wanders | G01N 1/30 435/29 |
| 2018/0012062 | A1* | 1/2018 | Zahniser | G01N 15/1433 |
| 2018/0017480 | A1* | 1/2018 | Fukuda | G01N 1/14 |
| 2020/0160094 | A1* | 5/2020 | Fujimoto | G06V 20/69 |
| 2021/0374952 | A1* | 12/2021 | Shafiee | C12M 23/16 |
| 2022/0291199 | A1 | 9/2022 | Asada et al. | |
| 2022/0291200 | A1 | 9/2022 | Asada et al. | |
| 2022/0292855 | A1 | 9/2022 | Asada et al. | |
| 2023/0221238 | A1 | 7/2023 | Asada et al. | |
| 2024/0386554 | A1* | 11/2024 | Fujimoto | G01N 33/493 |

FOREIGN PATENT DOCUMENTS

| | | | |
|---|---|---|---|
| JP | 2020-085535 | A | 6/2020 |
| WO | 2010/139697 | A1 | 12/2010 |
| WO | 2018/039216 | A1 | 3/2018 |

* cited by examiner (CONT.)

(FIG. 6 CONTINUED)
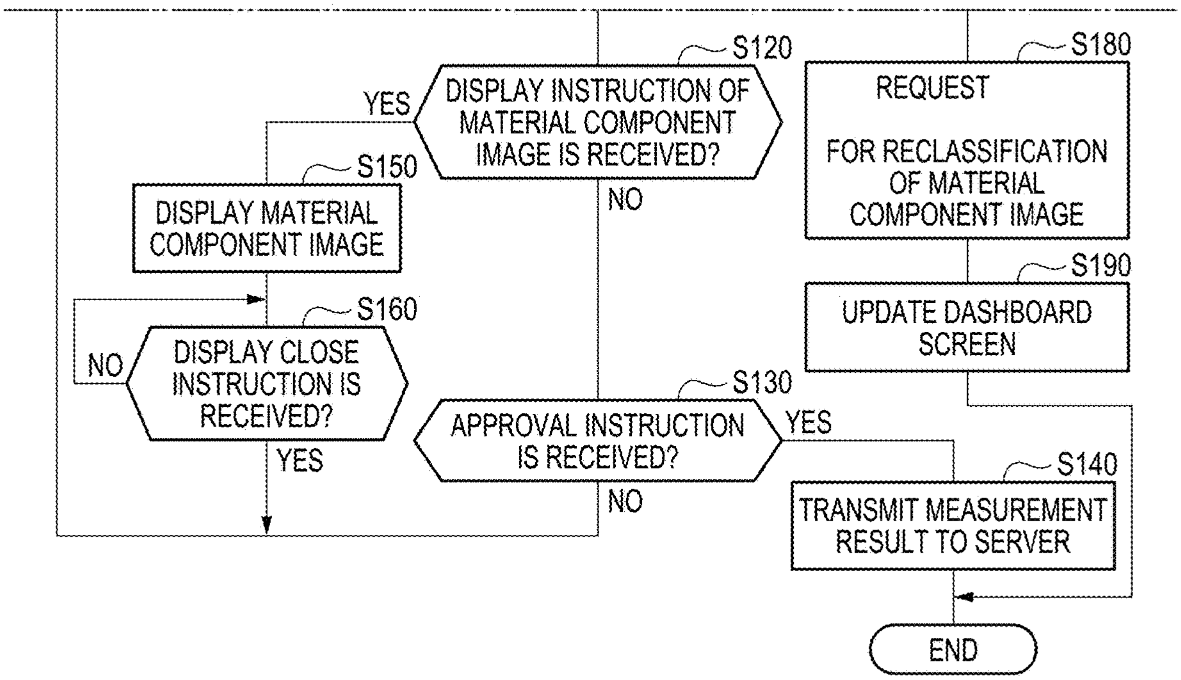

DETERMINING MATERIAL COMPONENT CONCENTRATIONS IN A SAMPLE

CROSS-REFERENCES TO RELATED APPLICATIONS

This application claims priority to Japan Patent Application Nos. 2023-081856 and 2023-081902, each of which was filed on May 17, 2023, and each of which is incorporated herein in its entirety by reference.

TECHNICAL FIELD

The present disclosure relates determining material component concentrations in a sample, and more particularly relates to improving the classification of material components within a biological sample to improve the determination of material component concentrations.

BACKGROUND

Devices for material component classification for determining material component concentrations are known, which obtain images of a sample flowing through a flow cell. A material component image is classified based on a material component of the sample that is detected within the image. Through this classification, a concentration of each material component in the sample can be measured.

SUMMARY

When the measured concentration of the material component is an abnormal value, or some other condition is met or not met, there may be a problem in the classification of the material component images. Therefore, reclassification of a material component image may be necessary. It may be difficult to determine whether reclassification of a material component image is necessary.

The present disclosure provides methods and apparatuses that support the determination of whether reclassification of one or more material component images is necessary and hence improve the concentration determinations of a sample.

Moreover, the reclassification described herein may be used to improve the initial classification process and hence improve the concentration determinations of a sample (e.g., by using the reclassification information to train the classifier of the initial classification process).

An aspect of the present disclosure is an apparatus for determining material component concentrations in a sample. The apparatus includes an imaging device for imaging a sample including material components to produce sample images, an acquisition unit configured to acquire material component images of respective material components from at least some of the sample images, and a classification unit configured to classify the material component images into respective groups corresponding to a respective type of material component of the material components shown within a material component image. A concentration of the material component in the sample is based on a cardinality of the material component images classified into a group of the groups corresponding to the material component. The apparatus also includes an acceptance unit configured to determine whether a condition is satisfied indicating that reclassification of at least some of the material component images is recommended, a control unit configured to, when the condition is satisfied, transmit the at least some of the material component images as classified are transmitted to a remote processing device through a network, the remote processing device configured to reclassify the at least some of the material component images and return reclassification information for the at least some of the material component images, and a calculation unit configured to calculate a concentration of at least one material component of the material components in the sample using the reclassification information (e.g., using the groups resulting from the reclassification).

In some implementations of the apparatus, the control unit is configured to transmit the at least some of the material component images when at least one of a qualitative test result of the sample obtained by a qualitative analysis device configured to execute qualitative measurement of the sample satisfies the condition or error information in which an abnormality occurring in the qualitative analysis device is recorded satisfies the condition.

In some implementations of the apparatus, the control unit is configured transmit the at least some of the material component images only when the condition is satisfied and data transmission to the remote processing device is permitted in advance.

In some implementations of the apparatus, the control unit is configured to transmit a respective classification result of the at least some of the material component images to the remote processing device through the network together with the at least some of the material component images.

In some implementations of the apparatus, the calculation unit is configured to calculate a concentration of respective ones of the material components in the sample using the groups.

In some implementations of the apparatus, an updated model for the classification unit is trained using results from the classification unit and the reclassification information.

An aspect of the present disclosure is a system for determining material component concentrations in a sample. The system includes any apparatus described above as a first processing device and the remote processing device as a second processing device connected to the first processing device through the network. The second processing device includes a reclassification unit configured to reclassify a material component image among the at least some of the material component images received from the first processing device into a group corresponding to a type of a material component different from that determined by the classification unit, and a return unit configured to return a reclassification result of the material component image reclassified by the reclassification unit to the first processing device.

In some implementations of the system, the reclassification unit comprises a trained machine-learning model.

An aspect of the present disclosure is a method for determining material component concentrations in a sample. The method includes imaging, using an imaging device, a sample including material components to produce sample images, acquiring, using an acquisition unit, material component images of respective material components from at least some of the sample images, and classifying, using a classification unit, the material component images into respective groups corresponding to a respective type of material component of the material components shown within a material component image. A concentration of a material component in the sample is based on a cardinality of the material component images classified into a group of the groups corresponding to the material component. The method also includes determining, using an acceptance unit, that a condition is satisfied indicating that reclassification of at least some of the material component images is recommended, using a control unit and responsive to the determining, transmitting the at least some of the material component images as classified through a network to a remote processing device configured to reclassify the at least some of the material component images and return reclassification information for the at least some of the material component images, and calculating, using a calculation unit, a concentration of at least one material component of the material components in the sample using the reclassification information.

In some implementations of the method, executing the control results in transmitting all of the material component images as classified through the network to the remote processing device.

An aspect of the present disclosure is a non-transitory storage medium storing instructions that cause a processor to execute a process for determining material component concentrations in a sample. The process includes acquiring material component images of respective material components from at least some sample images obtained by imaging a sample including material components, classifying the material component images into respective groups corresponding to a respective type of material component of the material components shown within a material component image, wherein a concentration of the material component in the sample is based on a cardinality of the material component images classified into a group of the groups corresponding to the material component, determining that a condition is satisfied indicating that reclassification of at least some of the material component images is recommended, responsive to the determining, transmitting the at least some of the material component images as classified through a network to a remote processing device configured to reclassify the at least some of the material component images and return reclassification information for the at least some of the material component images, and calculating a concentration of at least one material component of the material components in the sample using the reclassification information.

In any of the above aspects, the condition may be represented by at least one of a magnitude relationship between a concentration of a material component of a type designated by a user and a threshold designated by a user, a magnitude relationship between a value of a qualitative item designated by a user among qualitative items in the qualitative test result of the sample and a threshold in the qualitative item, or an occurrence status of an error item designated by a user among error items in the error information.

In any of the above aspects, the condition may include at least one of a flag condition corresponding to an error that can occur in at least one of imaging the sample, acquiring the material component images, or classifying the material component images, a material component condition corresponding to a concentration value for at least one material component of the material components that is calculated before the determining, or a qualitative condition corresponding to a qualitative test result for at least one material component of the material components.

In any of the above aspects, a respective concentration of the material components in the sample using the groups may be initially calculated by the calculation unit.

An aspect of the present disclosure is another (e.g., a second) apparatus for determining material component concentrations in a sample. The apparatus includes an imaging device for imaging a sample including material components to produce sample images, an acquisition unit configured to acquire material component images of respective material components from at least some of the sample images, and a classification unit configured to classify the material component images into respective groups corresponding to a respective type of material component of the material components shown within a material component image, wherein a concentration of the material component in the sample is based on a cardinality of the material component images classified into a group of the groups corresponding to the material component. The apparatus also includes a transmission unit configured to transmit at least one material component image of the material component images as classified to a remote processing device through a network, the remote processing device configured to reclassify the at least one material component image and return reclassification information for the at least one material component image, and an output unit configured to output at least one of a first status, a second status, or a third status for a respective material component image of the at least one material component image, the first status representing a status after the classification unit classifies the material component image and representing a status of waiting for an instruction to transmit the material component image to the remote processing device, the second status representing a status of waiting to receive the reclassification information from the remote processing device, and the third status representing a status where the reclassification information for the material component image is received from the remote processing device.

In some implementations of the second apparatus, the apparatus also includes a calculation unit configured to calculate a concentration of at least one material component of the material components in the sample using the reclassification information. In some variations of these implementations, an updated model for the classification unit is trained using results from the classification unit and the reclassification information.

In some implementations of the second apparatus, the apparatus includes a reception unit configured to receive the reclassification information from the remote processing device.

In some implementations of the second apparatus, the third status includes a fourth status representing a status where the reclassification information is received from the remote processing device and the reclassification information does not include a recommendation to perform a predetermined test, and a fifth status representing a status where the reclassification information is received from the remote processing device and the reclassification information includes a recommendation to perform the predetermined test.

The predetermined test may include microscopy.

An aspect of the present disclosure is another (e.g., a second) system for determining material component concentrations in a sample. The system includes any one of the implementations of the second apparatus as a first processing device, and the remote processing device as a second processing device connected to the first processing device through the network. The second processing device can includes a reclassification unit configured to reclassify a material component image among the at least some of the material component images received from the first processing device into a group corresponding to a type of a material component different from that determined by the classification unit, and a return unit configured to return a reclassification result of the material component image reclassified by the reclassification unit to the first processing device.

In some implementations of the second system, the reclassification unit comprises a trained machine-learning model.

An aspect of the present disclosure is a (e.g., second) method for determining material component concentrations in a sample. The method includes imaging, using an imaging device, a sample including material components to produce sample images, acquiring, using an acquisition unit, material component images of respective material components from at least some of the sample images, and classifying, using a classification unit, the material component images into respective groups corresponding to a respective type of material component of the material components shown within a material component image, wherein a concentration of the material component in the sample is based on a cardinality of the material component images classified into a group of the groups corresponding to the material component. The method also includes transmitting, using a transmission unit, at least one material component image of the material component images as classified to a remote processing device through a network, the remote processing device configured to reclassify the at least one material component image and return reclassification information for the at least one material component image, and outputting, using an output unit, at least one of a first status, a second status, or a third status for a respective material component image of the at least one material component image, the first status representing a status after the classification unit classifies the material component image and representing a status of waiting for an instruction to transmit the material component image to the remote processing device, the second status representing a status of waiting to receive the reclassification information from the remote processing device, and the third status representing a status where the reclassification information for the material component image is received from the remote processing device.

In some implementations of the second method, transmitting the at least one material component image comprises transmitting all of the material component images as classified through the network to the remote processing device.

In some implementations of the second method, the method includes calculating, using a calculation unit, a concentration of at least one material component of the material components in the sample using the reclassification information.

In some implementations of the second method, the method includes calculating, using a calculation unit, a respective concentration of the material components in the sample using the groups before receiving the reclassification information.

In any of the second apparatus, the second system, or the second method, the output unit may be a display unit. The display unit may display each of the first status, the second status, and the third status for multiple samples.

As aspect of the present disclosure includes a second non-transitory storage medium storing instructions that cause a processor to execute a process for determining material component concentrations in a sample. The process includes imaging a sample including material components to produce sample images, acquiring material component images of respective material components from at least some of the sample images, and classifying the material component images into respective groups corresponding to a respective type of material component of the material components shown within a material component image, wherein a concentration of the material component in the sample is based on a cardinality of the material component images classified into a group of the groups corresponding to the material component. The process also includes transmitting at least one material component image of the material component images as classified to a remote processing device through a network, the remote processing device configured to reclassify the at least one material component image and return reclassification information for the at least one material component image, and outputting at least one of a first status, a second status, or a third status for a respective material component image of the at least one material component image, the first status representing a status after the classification unit classifies the material component image and representing a status of waiting for an instruction to transmit the material component image to the remote processing device, the second status representing a status of waiting to receive the reclassification information from the remote processing device, and the third status representing a status where the reclassification information for the material component image is received from the remote processing device.

In any of these aspects, the sample may be urine.

In any of these aspects, the reclassification information may include at least one material component different from the respective types of material components available for the classifying into the groups.

These aspects and additional variations thereof are described below in the specification, claims, and appended drawings.

DETAILED DESCRIPTION

Figure 1:
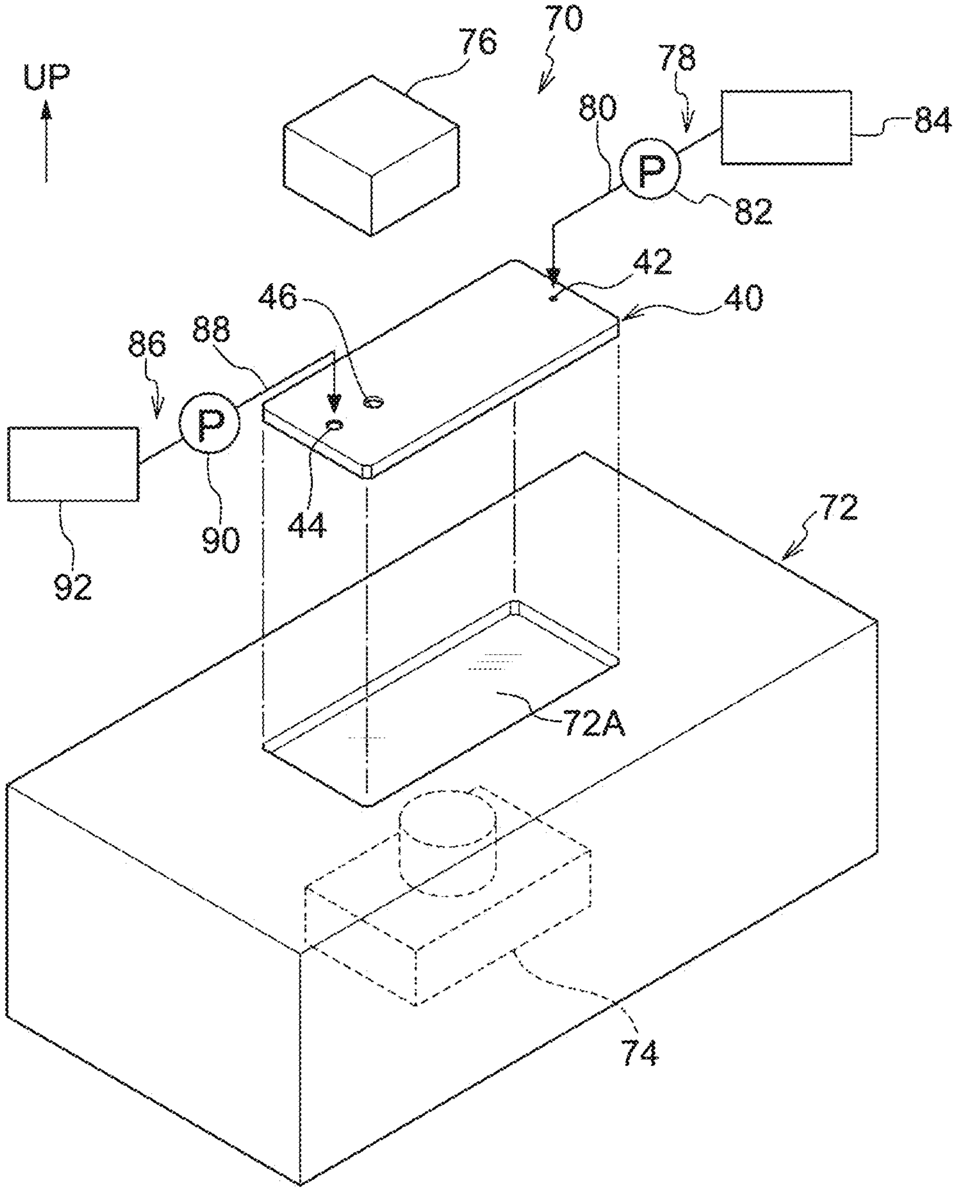
FIG. 1 is a perspective view illustrating an example of a configuration of a urinary material component analysis device for determining material component concentrations according to an embodiment of the teachings herein.

Hereinafter, embodiments of the present disclosure will be described in detail with reference to the drawings. Components and processes having the similar operation, action, or function are represented by the same reference numerals in all the drawings, and duplicative description will be omitted as appropriate. In each of the drawings, the present disclosure is schematically illustrated to the extent that the disclosure can be sufficiently understood. The teachings herein are not limited to the illustrated examples. In this description, a configuration that does not directly relate to the present disclosure or a well-known configuration may be omitted.

FIG. 1 is a perspective view illustrating an example of a configuration of a urinary material component analysis device 70 for determining material component concentrations according to an embodiment of the teachings herein.

As illustrated in FIG. 1, the urinary material component analysis device 70 includes a flow cell 40, a housing 72, a camera 74, and a light source 76. Arrow UP in FIG. 1 indicates the upper side in a vertical direction of the urinary material component analysis device 70.

The flow cell 40 is applicable to a urinary material component test (urinary sediment test) in which, by introducing a urine sample as an example of a sample together with a sheath fluid, material components in the urine sample are imaged by the camera 74 to execute various analyses from the shape or the like of the material components of the obtained images. The camera 74 is an example of an imaging unit. The urine sample can include multiple different types of material components. Examples of the types of material components include red blood cells, white blood cells, epidermal cells, casts, and bacteria. In this example where a urinary material component test, each of red blood cells, white blood cells, non-squamous epidermal cells, squamous epidermal cells, bacteria, crystals, yeast, hyaline casts, other casts (also referred to as pathological casts), mucus, spermatozoa, and white blood cell clumps in the urine sample is set as a target to be measured, and a concentration of a target urinary material component in urine is measured. However, the urinary material component analysis device 70 is one example of a material component analysis device that may be used for material component classification according to the teachings herein. Accordingly, the description herein applies to a material component test for blood, cells, body fluids, and the like as test objects or samples.

In the urinary material component analysis device 70, the flow cell 40 is disposed in the housing 72. A recessed portion 72A is formed in the housing 72, and the flow cell 40 is inserted into the recessed portion 72A. Aa portion of the housing 72 at a position including the recessed portion 72A is formed of a transparent member (for example, glass). In the housing 72, the camera 74 is provided at a position facing the flow cell 40. Above the housing 72, the light source 76 is provided at a position facing the camera 74 with the flow cell 40 interposed therebetween. The camera 74 is disposed at a position where a sample fluid flowing through the flow cell 40 can be imaged.

The urinary material component analysis device 70 includes a first supply device 78 that supplies the sample fluid into a sample introduction port 42 of a sample flow path (not illustrated) in the flow cell 40. The first supply device 78 includes a supply tube 80 having one end portion connected to the sample introduction port 42. The first supply device 78 also includes a pump 82 that is provided (e.g., halfway) along the supply tube 80. A source for the sample fluid is connected to the other end portion of the supply tube 80. In this example, a spitz tube 84 that stores the sample fluid is disposed in the other end portion of the supply tube 80. A barcode label displaying a barcode representing a sample ID for uniquely identifying the sample in the spitz tube 84 may be attached to a side surface of the spitz tube 84.

The urinary material component analysis device 70 includes a second supply device 86 that supplies sheath fluid into a sheath introduction port 44 of a sheath flow path (not illustrated) in the flow cell 40. The second supply device 86 includes a supply tube 88 having one end portion connected to the sheath introduction port 44, a pump 90 that is provided (e.g., halfway) along the supply tube 88, and a tank 92 that is connected to the other end portion of the supply tube 88 for storing the sheath fluid. In some implementations of a material component analysis device, the second supply device 86 may be omitted or may supply a different fluid for support of material component classification of a sample. In some implementations, two or more supply devices may be used in addition to the sample first supply device 78 that supplies the sample.

In the flow cell 40, a discharge port 46 is provided between the sample introduction port 42 and the sheath introduction port 44. A discharge tube (not illustrated) is connected to one end portion of the discharge port 46, and a waste tank (not illustrated) is connected to the other end portion of the discharge tube 46. The flow cell 40 may include a junction portion where the sample introduced from the sample introduction port 42 and the sheath fluid introduced from the sheath introduction port 44 are joined such that joined fluid flows in the flow path. Material components in the sample flow are imaged by the camera 74.

Figure 2:
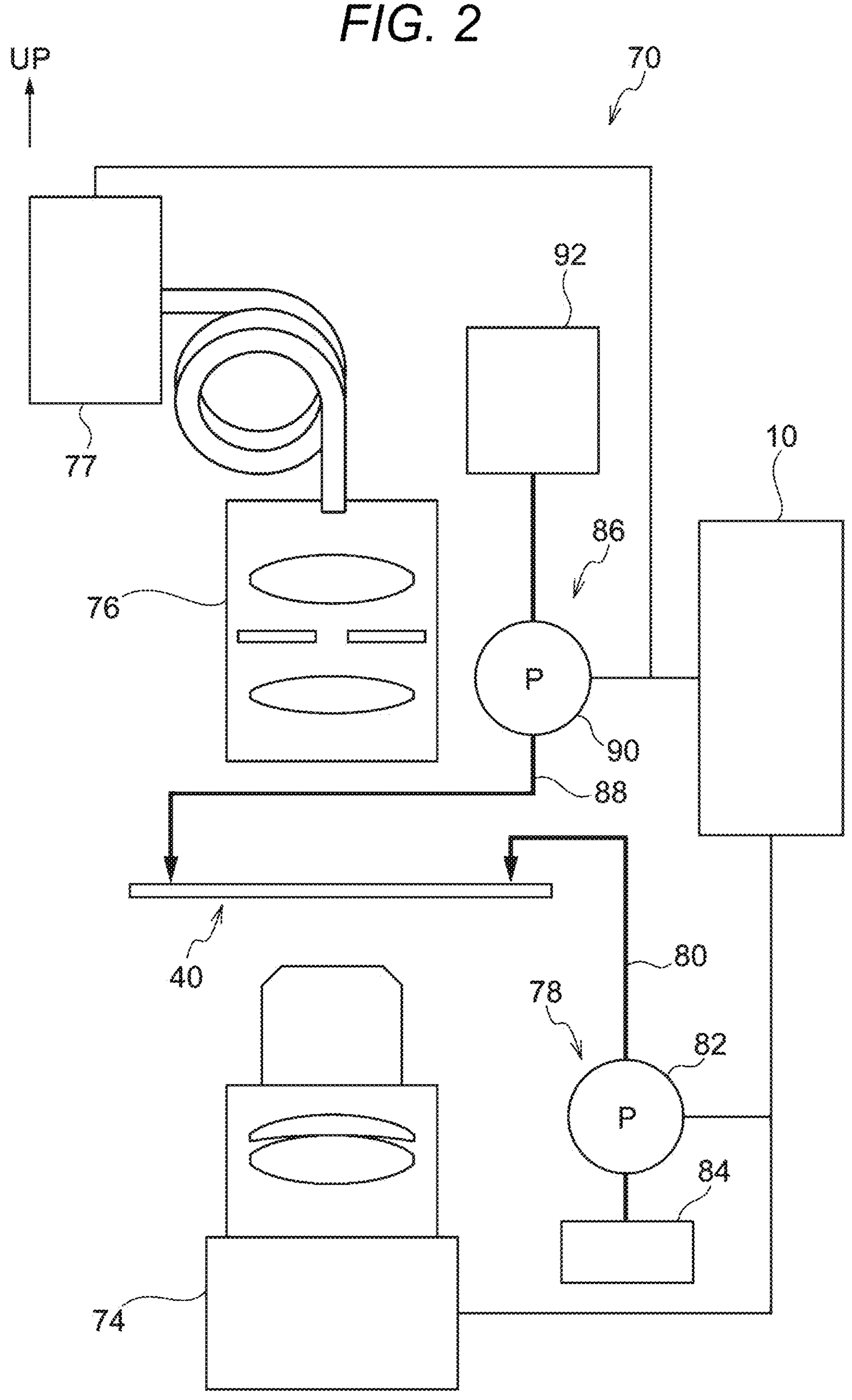
FIG. 2 is a side view illustrating the urinary material component analysis device according to FIG. 1.

FIG. 2 is a side view illustrating the urinary material component analysis device 70 according to FIG. 1.

As illustrated in FIG. 2, the urinary material component analysis device 70 includes a first processing device 10. As in FIG. 1, the arrow UP in FIG. 2 indicates the upper side in the vertical direction of the urinary material component analysis device 70.

The first processing device 10, described in more detail below, controls each of operations of the camera 74, a light source operating unit 77 that is electrically connected to the light source 76, the pump 82, and the pump 90. The first processing device 10 causes the light source 76 to emit light at predetermined intervals by applying a pulse signal to the light source operating unit 77. The first processing device 10 drives the pump 82 to control the flow rate of the sample, and drives the pump 90 to control the flow rate of the sheath fluid. Although not illustrated in FIG. 2, the first processing device 10 may include a plurality of cameras 74 and an optical system that guides light to each of the cameras 74. The optical system is adjusted such that the cameras 74 are in focus at different positions (depths) in the flow cell 40, respectively. In this way, a plurality of images that are in focus at the same position on a horizontal plane and at different depth positions may be simultaneously obtained by the plurality of cameras 74. The simultaneously obtained images are stored in a storage unit 15 illustrated in FIG. 3 and described below. The depth direction described herein refers to a direction perpendicular to a direction in which the sample flows, and refers to the vertical direction in FIG. 2. In this implementation, distances between each focal point and a wall surface of the flow cell 40 on a side closer to the cameras 74 are different.

Figure 3:
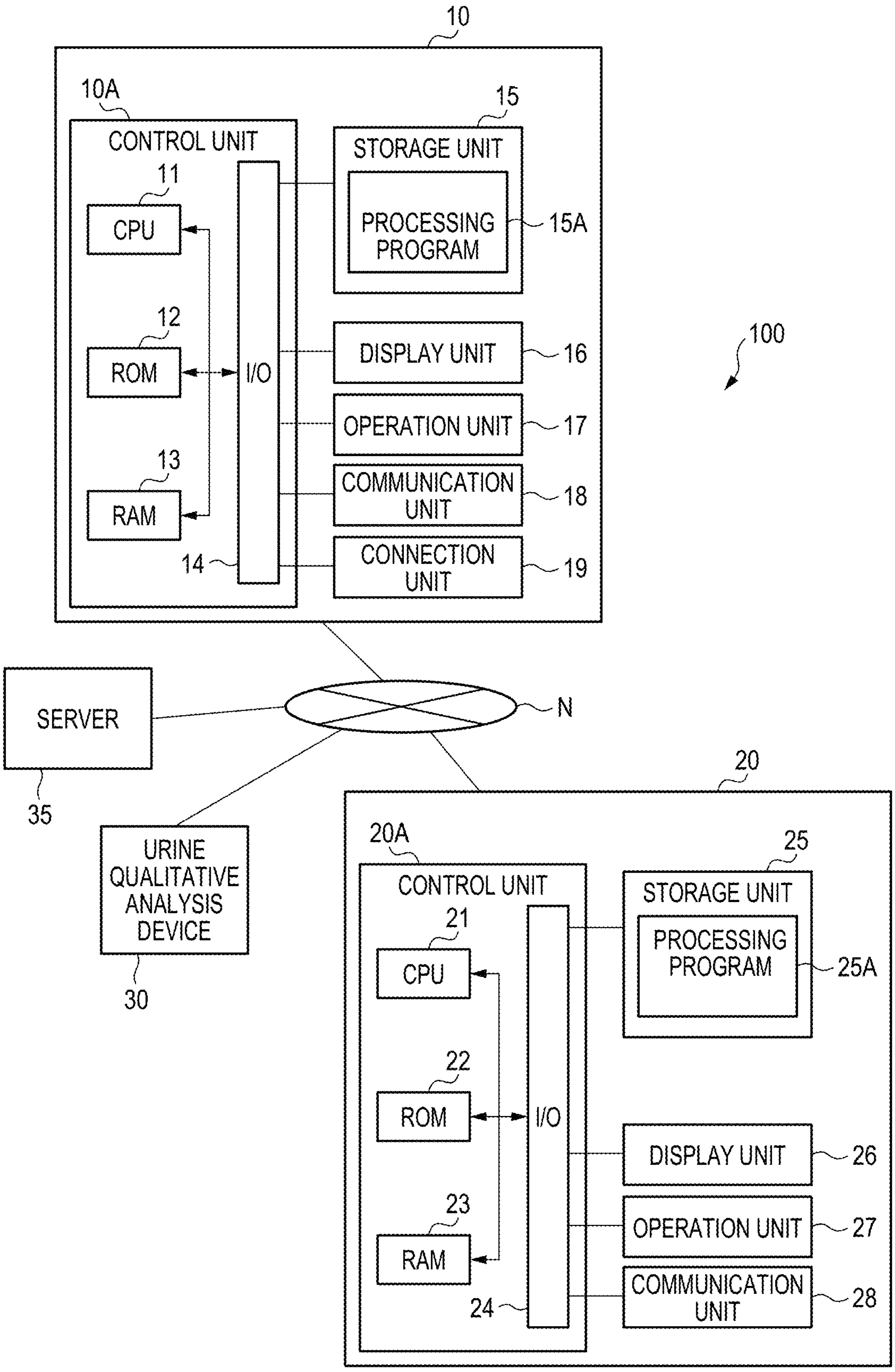
FIG. 3 is a block diagram illustrating an example of a material component processing system according to an embodiment of the teachings herein.

FIG. 3 is a block diagram illustrating an example of a material component processing system 100 according to an embodiment of the teachings herein.

As illustrated in FIG. 3, the material component processing system 100 includes the first processing device 10, a remote or second processing device 20, a qualitative analysis device that executes qualitative measurement of a sample, in this example a urine qualitative analysis device 30, and a server 35. The first processing device 10 and the qualitative analysis device are connected to the second processing device 20 through a network N, and the qualitative analysis device is linked with a material component analysis device. In the example of FIG. 3, the urine qualitative analysis device 30 is linked with the urinary material component analysis device 70.

The first processing device 10 includes a central processing unit (CPU) 11, a read-only memory (ROM) 12, a random-access memory (RAM) 13, an input/output interface (I/O) 14, the storage unit 15, a display unit 16, an operation unit 17, a communication unit 18, and a connection unit 19. The CPU 11 may be, for example, a processor such as a graphics processing unit (GPU). The first processing device 10 can include fewer hardware components, different hardware components, or more hardware components than those shown by example.

The first processing device 10 may be or be a part of a general-purpose computer device such as a personal computer (PC). The first processing device 10 may be or be part of a portable computer device such as a smartphone or a tablet terminal. The first processing device 10 and/or its functions described herein may be divided into a plurality of units. For example, the first processing device 10 may include a first unit that controls a measurement system such as the camera 74, the light source 76, the pump 82, and the pump 90 as described above and a second unit that processes and analyzes the images obtained by the camera 74. The first processing device 10 may be externally connected to a material component analysis device. That is, while the first processing device 10 may be internal to a material component analysis device, at least in part, such as in the housing 72 of the urinary material component analysis device 70, the first processing device 10 or portions thereof may be externally located and connected by cables, etc., to the material component analysis device.

A control unit 10A may be formed of the CPU 11, the ROM 12, the RAM 13, and the I/O 14. In some implementations, the control unit 10A has a function of controlling a measurement system such as the camera 74, the light source 76, the pump 82, and the pump 90. In some implementations, the control unit 10A has a function of processing (examining, analyzing, inspecting, etc.) images obtained by the camera 74. The CPU 11, the ROM 12, the RAM 13, and the I/O 14 may be connected to each other through a bus.

Respective functional units including the storage unit 15, the display unit 16, the operation unit 17, the communication unit 18, and the connection unit 19 are connected to the I/O 14. The functional units can communicate with the CPU 11 through the I/O 14.

The control unit 10A may be a sub-control unit that controls a part of the operation of the first processing device 10 or may be a part of a main control unit that controls the overall operation of the first processing device 10. As a part or all of each block of the control unit 10A, for example, an integrated circuit such as large scale integration (LSI) or an integrated circuit (IC) chip set may be used. As the respective blocks, individual circuits may be used, or an integrated circuit where a part or all of the blocks are integrated may be used. The respective blocks may be integrally provided, or a part of the blocks may be separately provided. A part of each of the blocks may be separately provided. The integration of the control unit 10A is not limited to the LSI, and a dedicated circuit or a general-purpose processor may be used. At least some of the functions of the control unit 10A may be performed using software instructions stored in a non-transitory storage medium, such as the storage unit 15.

As the storage unit 15, for example, a hard-disk drive (HDD), a solid-state drive (SSD), a flash memory, or some combination thereof is used. The storage unit 15 stores a processing program 15A for executing a measurement process and a remeasurement process described below. The processing program 15A may be stored in the ROM 12 and may also be referred to as a first processing program. As the storage unit 15, a memory may be externally attached, or may be subsequently expanded.

The processing program 15A may be installed in advance in, for example, the first processing device 10. The processing program 15A may be implemented by being stored in a nonvolatile non-transitory storage medium or by being distributed through the network N and being appropriately installed or upgraded in the first processing device 10. Examples of the nonvolatile non-transitory storage medium include a compact disc read-only memory (CD-ROM), a magneto-optical disk, an HDD, a digital versatile disc read-only memory (DVD-ROM), a flash memory, a memory card, or some combination thereof.

The display unit 16 is, for example, a liquid crystal display (LCD) or an organic electro luminescence (EL) display. The display unit 16 may integrally include a touch panel. In the operation unit 17, for example, a device such as a keyboard or a mouse for inputting an operation is provided. A user can transmit an instruction to the first processing device 10 by operating the operation unit 17. The display unit 16 displays the result of a process that is executed according to instructions received from the user or various types of information such as notifications for the process.

The communication unit 18 is connected to the network N such as the Internet, a local area network (LAN), a wide area network (WAN), or any combination thereof. The communication unit 18 can communicate with the second processing device 20 through the network N wirelessly, through one or more communication wires, or any combination thereof.

In some implementations, the connection unit 19 connects the measurement system, such as the camera 74, the light source 76, the pump 82, and the pump 90, to the first processing device 10. The measurement system is controlled by the control unit 10A described above. The connection unit 19 also functions as an input port through which the images output from the camera 74 are input.

The second processing device 20 according to the present embodiment includes a CPU 21, a ROM 22, a RAM 23, an input/output interface (I/O) 24, a storage unit 25, a display unit 26, an operation unit 27, and a communication unit 28. The CPU 21 may be, for example, a processor such as a GPU. The second processing device 20 can include fewer hardware components, different hardware components, or more hardware components than those shown by example.

The second processing device 20 may be or be a part of a general-purpose computer device such as a PC. The second processing device 20 may be or be part of a portable computer device such as a smartphone or a tablet terminal. The second processing device 20 generally executes a larger amount of data processing than the first processing device 10. Thus, and while not necessary, it is advantageous that the access speed of the memory in the second processing device 20 is faster than that of the memory in the first processing device 10, and it is advantageous that the processing speed of the CPU 21 in the second processing device 20 is faster than that of the CPU 11 in the first processing device 10.

A control unit 20A may be formed of the CPU 21, the ROM 22, the RAM 23, and the I/O 24. The respective units including the CPU 21, the ROM 22, the RAM 23, and the I/O 24 are connected to each other through a bus.

Respective functional units including the storage unit 25, the display unit 26, the operation unit 27, and the communication unit 28 are connected to the I/O 24. The functional units can communicate with the CPU 21 through the I/O 24.

As the storage unit 25, for example, an HDD, an SSD, a flash memory, or some combination thereof is used. The storage unit 25 stores a processing program 25A for executing a reclassification process described below. The processing program 25A may be stored in the ROM 22 and may be referred to as a second processing program. As the storage unit 25, a memory may be externally attached, or may be subsequently expanded.

The processing program 25A may be installed in advance in, for example, the second processing device 20. The processing program 25A may be implemented by being stored in a nonvolatile non-transitory storage medium or by being distributed through the network N to be appropriately installed or upgraded in the second processing device 20. Examples of the nonvolatile non-transitory storage medium include a CD-ROM, a magneto-optical disk, an HDD, a DVD-ROM, a flash memory, a memory card, or some combination thereof.

The display unit 26 is, for example, an LCD or an organic EL display. The display unit 26 may integrally include a touch panel. In the operation unit 27, for example, a device such as a keyboard or a mouse for inputting an operation is provided. The user transmits an instruction to the second processing device 20 by operating the operation unit 27. The display unit 26 displays the result of a process that is executed according to instructions received from the user or various types of information such as notifications for the process.

The communication unit 28 is connected to the network N, such as the Internet, a LAN, a WAN, or any combination thereof. The communication unit 28 can communicate with the first processing device 10 through the network N wirelessly, through one or more communication wires, or any combination thereof.

In this example, the urine qualitative analysis device 30 and the urinary material component analysis device 70 are linked through a transport path of the urine sample. The urine qualitative analysis device 30 is a device for executing a urine qualitative test for the urine sample. The urine qualitative test is, for example, a test in which test paper called tes-tape of which the color changes by reacting with a target component in the urine sample is dipped in the urine to measure a change in color to determine whether the target component is present in the urine sample or to measure the concentration of the component to be measured in the urine sample. Although not shown, the urine qualitative analysis device 30 may include a barcode reader for reading the sample ID of the sample to be measured from the barcode label attached to the side surface of the spitz tube 84, and the urine qualitative test result of the urine sample tested by the urine qualitative analysis device 30 and the sample ID of the urine sample are linked (associated) with each other and are transmitted to the server 35 through the network N, e.g., for storage. When an error occurs during the measurement of the urine sample, the urine qualitative analysis device 30 links error information of the urine sample with the sample ID of the urine sample and transmits the linked information to the server 35 through the network N.

Next, a functional configuration of the first processing device 10 according to the present embodiment will be described in detail with reference to FIG. 4, which is a functional block diagram illustrating an example of the first processing device 10 according to FIG. 3.

Figure 4:
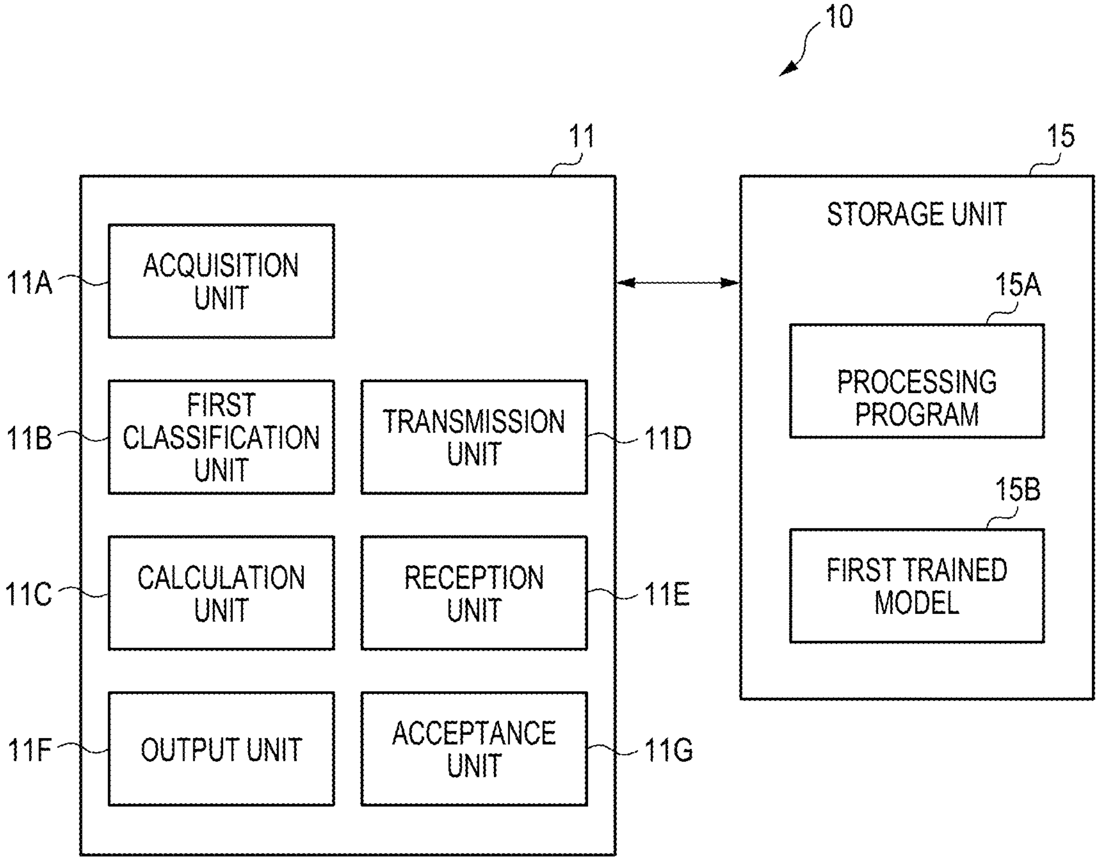
FIG. 4 is a functional block diagram illustrating an example of a first processing device according to FIG. 3.

In some implementations, the CPU 11 of the first processing device 10 may perform the functions of each of the units illustrated in FIG. 4 by writing the processing program 15A stored in the storage unit 15 into the RAM 13 and executing the processing program 15A.

As illustrated in FIG. 4, the CPU 11 of the first processing device 10 functions as an acquisition unit 11A, a first classification unit 11B, a calculation unit 11C, a transmission unit 11D, a reception unit 11E, an output unit 11F, and an acceptance unit 11G.

The camera 74 images the sample flowing through the flow cell 40 to obtain a plurality of image. From these sample images, for example 300 to 1000 images, the acquisition unit 11A extracts plural types of material components in the sample as material component images 3 (see FIG. 7). More specifically, the acquisition unit 11A extracts at least one material component image 3 from each of the sample images using any technique. In some implementations, image extraction may use an image processing technique such as binarization processing or contour extraction, a method using machine learning, a method using pattern matching, or any combination thereof. Desirably, although not necessary, each of the material component images 3 includes one material component. In these implementations, one material component is imaged in each of the material component images 3.

The first classification unit 11B classifies the material component images 3 acquired by the acquisition unit 11A into any of a number of predetermined classifications (e.g., that depend on the type of the sample). The classifications of the material components may include, for example, red blood cells (RBC), white blood cells (WBC), non-squamous epidermal cells (NSE), squamous epidermal cells (SQEC), bacteria (BACT), crystals (CRYS), yeast (YST), hyaline casts (HYST), other casts (NHC), mucus (MUCS), spermatozoa (SPRM), white blood cell clumps (WBCC), or material components other than the above-described examples, also called unclassified (UNCL). Unclassified components may result where different types of materials bind to each other, for example. Stated simply, the detected components classified into the predetermined classifications by the first classification unit 11B correspond to the material components thereof and the classification defined as unclassified.

To classify the material component images 3, a material component image group (or set) may be temporarily stored in the storage unit 15 for each sample. The first classification unit 11B may use any known technique such as a method using machine learning or a method using pattern matching for classification. In an example herein, the storage unit 15 may store a first trained model 15B used by the first classification unit 11B to classify the images.

The first trained model 15B is a model that is generated by machine learning training data obtained by associating previously obtained material component images with the characteristics of a detected component in each predetermined classification. The training data is labeled data that identifies characteristics of an image and the resulting classification. Some examples of labeled data may include the type, size, or shape of the material component within an image, whether a nucleus is present, or some combination thereof. In some implementations, a convolutional neural network (CNN) may be used as the training model for machine learning. In some implementations, deep learning may be used as a method of machine learning.

The first trained model 15B receives the material component images 3 as an input, identifies at least some of the labeled data as input, and outputs the detected component in a predetermined classification. The material component image group is configured by the individual material component images 3, and thus may also be referred to as the material component image group 3 using the same reference numeral as the material component images 3.

When the material component images 3 are classified, the first classification unit 11B calculates a degree of suitability based on the used image classification method (for example, machine learning or pattern matching). The first classification unit 11B classifies the material component images into, for example, a classification having the highest degree of suitability. The degree of suitability described herein refers to the classification probability for the images of the classification result. In some implementations, the classification probability may be a percentage in which an image in each predetermined classification matches with a correct image or a predetermined feature point increases. As the classification probability increases, a higher value is assigned to the degree of suitability of the image. When the image completely matches with the correct image or a feature point, the degree of suitability is 100%. Stated differently, a material component image 3 having a relatively low degree of suitability is not likely to be appropriately classified. The degree of suitability may be represented by a suitability ratio.

The value of the degree of suitability may change depending on the way that material components are imaged in the material component images 3. Specifically, in an image in which a material component is in focus, the material component may be easily determined based on a classification using machine learning or the like. The degree of suitability for an accurate classification is high, and the degree of suitability for an inaccurate classification is low. However, in an image in which a material component is not in focus, that is, in an image in which the material component is blurred, the degree of suitability for an accurate classification may be low, and a difference between the degree of suitability for the accurate classification and the degree of suitability for an inaccurate classification is also small. In an image in which a plurality of material components overlap each other, the degree of suitability may have a low value. To be exact, even in an item of a rare sample that should be determined as unclassified and that is not trained by the first trained model 15B, material components may be classified into some classification. Therefore, here, the degree of suitability has a low value.

The calculation unit 11C calculates the amount (e.g., a concentration) of a material component in the sample based on the number of material component images classified into each predetermined classification by the first classification unit 11B. The concentration may be a number concentration (e.g., a cardinality of the images classified with a particular material component or as described in additional detail below), a percentage per volume of the sample or portion of the sample, or some other measure.

As described below, when the remeasurement of the amount of the material component in the sample is necessary, the transmission unit 11D controls the communication unit 18 to transmit the material component images 3 to the second processing device 20 through the network N. The material component images 3 transmitted to the second processing device 20 may be all or a part of the classified material component images 3. The transmission unit 11D transmits the material component images 3 together with the classification result of the material component images 3 classified by the first classification unit 11B.

The reception unit 11E controls the communication unit 18 to receive a reclassification result of reclassifying a material component image 3 by the second processing device 20 as described in additional detail below. The reclassification result, when made, is received by the reception unit 11E from the second processing device 20.

The output unit 11F can output images and other information related to the classification of the first processing device 10, the reclassification of the second processing device 20, or both. In some implementations, the output described herein may be a display output by the display unit 16, a print output from a printer (not illustrated), some other output, such as audio, or any combination thereof.

In some implementations, the information received from the second processing device 20 from the reception unit 11E is stored at the first processing device 10, such as in the storage unit 15, together with other information related to the classification of the first processing device 10.

In some implementations, the measurement status of the material component images and/or the material component concentrations can be associated with statuses as "Ordered", "Not Approved", "Being Reviewed", "Waiting for Approval", "Waiting for Microscopy", "Confirmation Required", or some combination thereof as discussed in additional detail below. The output unit 11F can output at least one of a first status, a second status, or a third status for a respective material component image 3. For example, the first status can represent a status after the first classification unit 11B classifies a material component image 3 into a classification of the predetermined classifications. The first status can be or include the classification, the degree of suitability or level of confidence in the classification, an indicator of waiting for an instruction to transmit the material component image 3 to the second processing device 20, or any combination thereof (corresponding to "Not Approved" in some implementations). The second status can be an indicator of waiting for a reclassification result from the second processing device 20 (corresponding as "Being Approved" in some implementations). The third status can represent a status where the reclassification result is received from the second processing device 20. The third status can be or include the reclassification, the degree of suitability or level of confidence in the reclassification, an indicator that the reclassification has been received, or any combination thereof (corresponding to "Waiting for Approval" or "Waiting for Microscopy" in some implementations).

In some implementations, the third status may include a fourth status and a fifth status. The fourth status represents a status where the reclassification information is received from the second processing device 20 and the reclassification information does not include a recommendation to perform microscopy, which is an example of a predetermined test (and may correspond to "Waiting for Approval"). The fifth status represents a status where the reclassification information is received from the remote processing device 20 and the reclassification information includes a recommendation to perform the predetermined test (and may correspond to "Waiting for Microscopy").

The displayed statuses are not limited to the first status to the fifth status, and other statuses can be appropriately added. For example, a status indicating occurrence of error during the measurement may be added (and may correspond to "Confirmation Required"). The status "Ordered" may be used to indicate a sample for which the order is completed.

Accordingly, the status of the reclassification process can be easily grasped when material component images are reclassified using the second processing device.

The acceptance unit 11G receives an operation input from the user through the operation unit 17 as described in additional detail below with regards to FIG. 6.

Next, a functional configuration of the second processing device 20 according to FIG. 3 is described in detail with reference to FIG. 5, which is a functional block diagram illustrating an example of the second processing device 20 according to FIG. 3.

Figure 5:
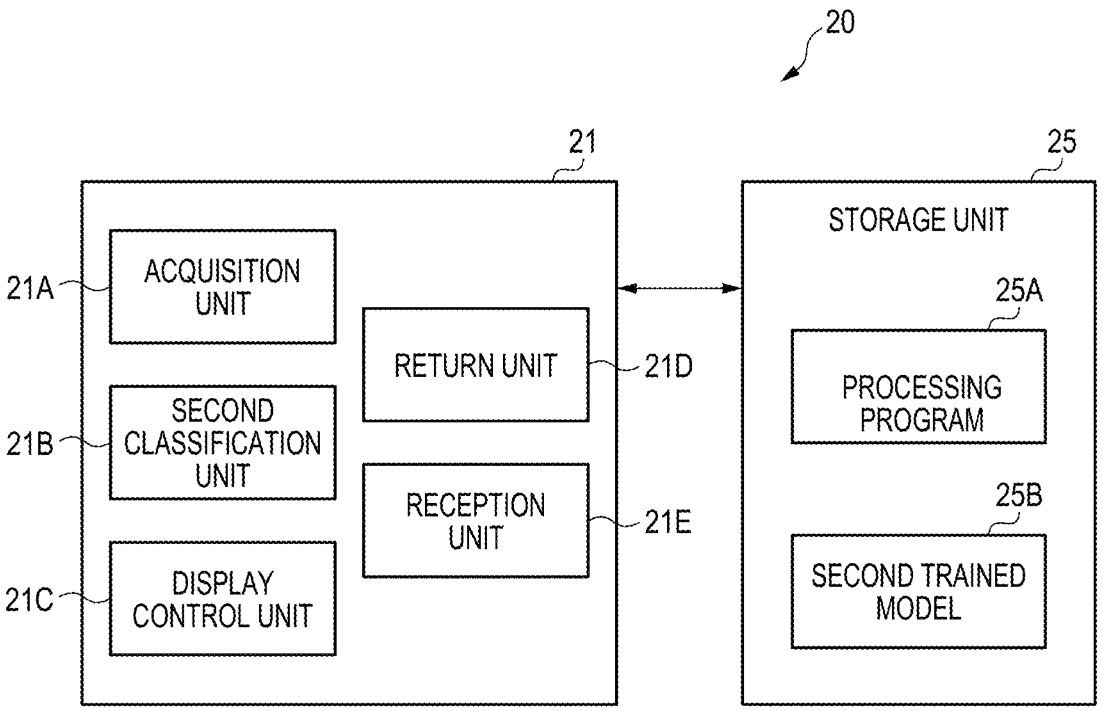
FIG. 5 is a functional block diagram illustrating an example of a second processing device according to FIG. 3.

In some implementations, the CPU 21 of the second processing device 20 may performs the functions of each of the units illustrated in FIG. 5 by writing the processing program 25A stored in the storage unit 25 into the RAM 23 and executing the processing program 25A.

As illustrated in FIG. 5, the CPU 21 of the second processing device 20 according to the present embodiment functions as an acquisition unit 21A, a second classification unit 21B, a display control unit 21C, a return unit 21D, and a reception unit 21E.

The reception unit 21E controls the communication unit 28 to receive one or more material component images 3 from the first processing device 10. The material component images 3 received from the first processing device 10 may be temporarily stored in the storage unit 25 as a classification target image group.

The acquisition unit 21A acquires the material component images 3 to be classified from the classification target image group stored in the storage unit 25.

The second classification unit 21B classifies the material component images 3 acquired by the acquisition unit 21A into any of the predetermined classifications used by the first classification unit 11B. The material component image 3 classified into any of the predetermined classifications by the second classification unit 21B is transmitted to the return unit 21D.

The second classification unit 21B may use any known technique such as a method using machine learning or a method using pattern matching for classification. Desirably, the accuracy of the technique used by the second classification unit 21B is higher than the accuracy of the technique used by the first classification unit 11B. For example, the amount of data used to train the machine learning or the pattern matching or other technique used by the second classification unit 21B is greater than that used for the first classification unit 11B.

In an example herein, the storage unit 25 stores a second trained model 25B used by the second classification unit 21B to reclassify the material component images 3 sent from the first processing device 10. The second trained model 25B is a model that may be generated by machine learning training data associated with a larger amount of detected components than the training data of the first trained model 15B using the same algorithm as the algorithm of machine learning of the first trained model 15B. The amount of the training data used to train the second trained model 25B is larger than the amount of the training data trained used to train the first trained model 15B. As a result, the second trained model 25B is trained such that the classification performance is higher than that of the first trained model 15B.

In addition to CNN as described above, various methods such as linear regression, regularization, decision tree, random forest, k-nearest neighbors (k-NN) algorithm, logistic regression, or support-vector machine (SVM) can be used as the algorithm of machine learning. For example, when the classification performance of a trained SVM model is more accurate than a trained CNN model, the trained CNN model may be adopted as the first trained model 15B, and the trained SVM model may be adopted as the second trained model 25B. Conversely, when the classification performance of a trained CNN model is more accurate than a trained SVM model, the trained SVM model may be adopted as the first trained model 15B, and the trained CNN model may be adopted as the second trained model 25B. For a comparison between the classification performances of the trained models, calculating and comparing index values representing the model performance (for example, an accuracy rate or a suitability ratio) may be used with a common set of test data prepared in advance.

It is advantageous that the latest version of the second trained model 25B be used. That is, the second trained model 25B may be updated over time as more training data becomes available. Further, the second trained model 25B may be replaced with a differently-trained model in the event the new model is more accurate than the model it is replacing.

In some implementations, the second classification unit 21B may classify the material component images 3 according to a classification operation of the user. For example, the second classification unit 21B can execute the classification according to an instruction of the user. It is advantageous where the user described herein is, for example, a laboratory technician well versed in the classification of material component images. Hereinafter, a user who operates the second processing device 20 may be referred to as "laboratory technician" to be distinguished from a user who operates the first processing device 10.

The display control unit 21C executes control such that the material component images 3, which are the subject of reclassification, may be associated with the classification result made by the first classification unit 11B for display by the display unit 26. The laboratory technician may reclassify material component images 3 that are classified into erroneous classifications among the material component images 3 displayed by the display unit 26 into appropriate classifications. Of course, the second classification unit 21B may also confirm the classification made by the first classification unit 11B, which is also referred to herein as reclassification. In either situation, the second classification unit 21B can classify and display or otherwise output the material component images 3 according to the reclassification operation.

Next, operations of the first processing device 10 according to an embodiment of the teachings herein will be described with reference to FIG. 6.

Figure 6:
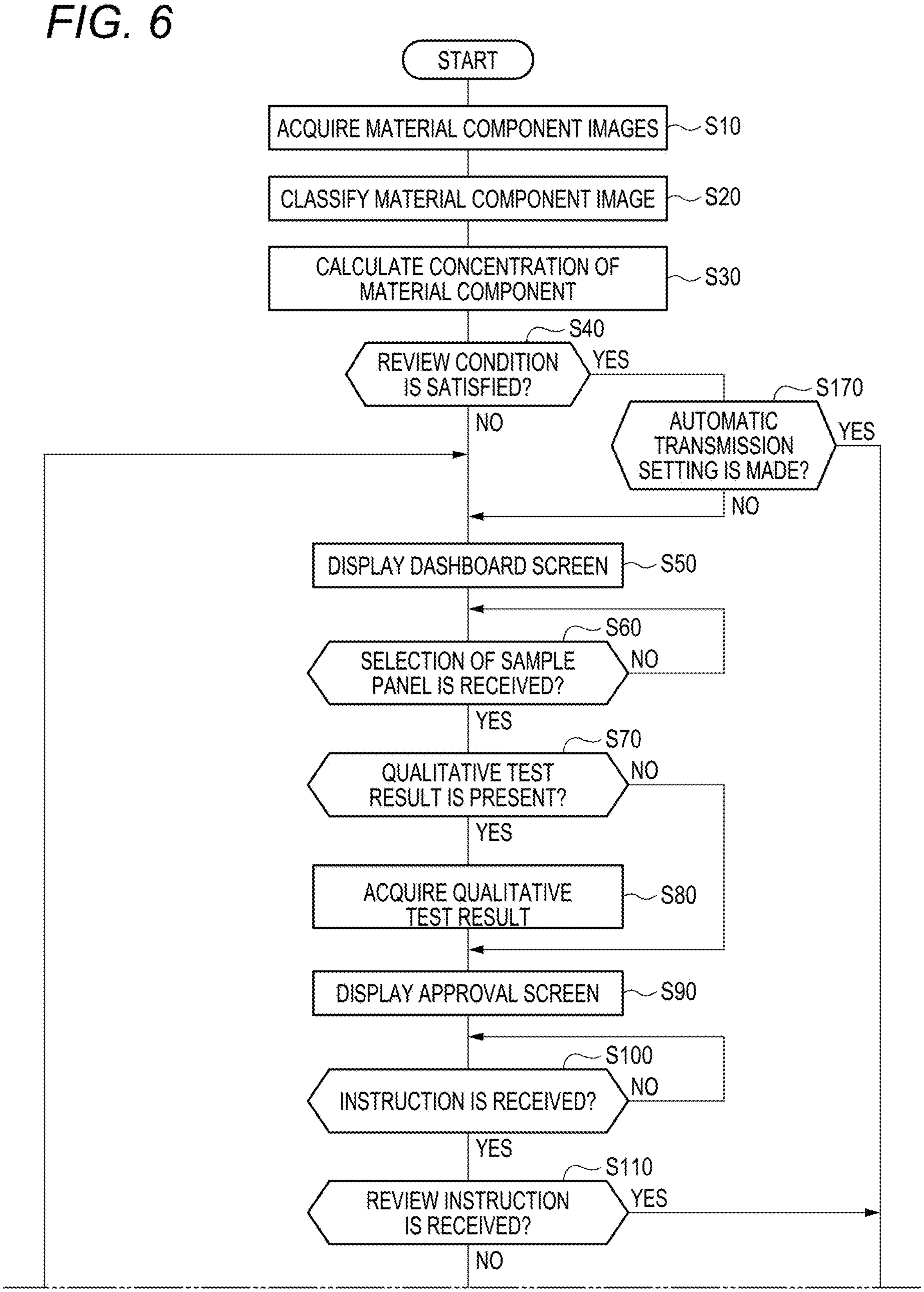
FIG. 6 is a flowchart diagram illustrating an example of a measurement process of the first processing device.

FIG. 6 is a flowchart diagram illustrating an example of a measurement process executed by the first processing device 10. The measurement process of FIG. 6 may start when the acceptance unit 11G receives an instruction to measure the sample from a user of the first processing device 10. The CPU 11 of the first processing device 10 can read the processing program 15A stored in the storage unit 15 and execute the measurement process.

At operation S10, the control unit 10A drives a transport unit (not illustrated) to transport the spitz tube 84 including the sample disposed at a predetermined position of the transport unit to a sample collection position. The control unit 10A can identify a sample ID of the current sample according to any known technique. For example, a barcode reader (not illustrated) may be attached to the sample collection position, and the control unit 10A can read the barcode label attached to the side surface of the spitz tube 84 using the barcode reader. In the barcode label, for example, the barcode representing the sample ID for uniquely identifying the sample is displayed, and the control unit 10A acquires the sample ID of the sample to be measured by reading the barcode label.

The control unit 10A moves the sample into a test position. In the illustrated example, the control unit 10A may control an actuator (not illustrated) that moves the supply tube 80 in the vertical direction of the urinary material component analysis device 70 such that a tip of the supply tube 80 (tip opposite to a tip connected to the sample introduction port 42) that is disposed above an opening portion of the spitz tube 84 transported to the sample collection position is lowered from the opening portion into the spitz tube 84. The control unit 10A drives the pump 82 after lowering the tip of the supply tube 80 to a position where the tip of the supply tube 80 reaches the sample. As a result, the sample in the spitz tube 84 is introduced from the sample introduction port 42 into the flow cell 40 at a predetermined flow rate such that a predetermined volume of the sample flows into the flow cell 40.

Meanwhile, the control unit 10A drives the pump 90 together with the driving of the pump 82. As a result, the sheath fluid stored in the tank 92 is introduced from the sheath introduction port 44 into the flow cell 40 at a predetermined flow rate such that the sheath fluid joins the sample in the flow cell 40.

The control unit 10A controls the camera 74 to obtain the sample image of the sample in the flow cell 40 and to store the obtained sample image in, for example, the storage unit 15. The number of the obtained sample images is not particularly limited. The user can change the cardinality of the obtained sample images to be stored (e.g., in the storage unit 15) through the operation unit 17.

The obtained sample images may respectively include various types of material components. Therefore, the acquisition unit 11A extracts the images of each of the material components in a sample image, that is, the material component images 3 for each of the material components within the sample image.

Figure 7:
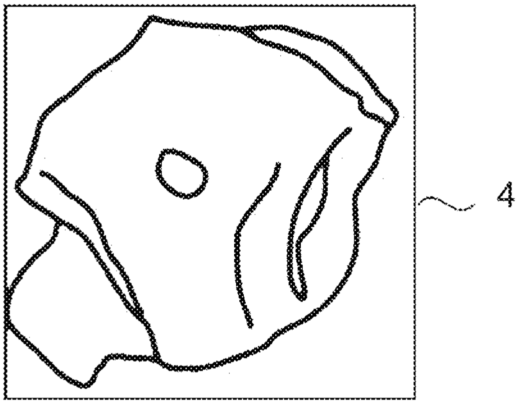
FIG. 7 is a diagram illustrating an example of a material component image.

FIG. 7 is a diagram illustrating an example of a material component image 3 extracted by the acquisition unit 11A. The material component image 3 may be a rectangular image that includes the entire material component no matter the shape of the material component. Accordingly, the size of the material component image 3 may change depending on the size of the material component.

The acquisition unit 11A allocates a material component image ID to each of the material component images 3 extracted from a sample image. The material component image ID is a unique identifier for each of the material component images 3. The material component image ID may be used as a file name of the material component image 3 in some implementations. The acquisition unit 11A may generate a classification list where each of the material component images 3 is associated with the sample ID of the sample from which the material component images 3 are obtained. The classification list may be stored in, for example, the storage unit 15. Table 1 shows an example of the classification list. The material component images 3 are images obtained from the same sample. Therefore, as shown in Table 1, the same sample ID is associated with the material component image IDs.

TABLE 1

| Sample ID | Material Component Image ID |
|---|---|
| #A0002 | #B00001 |
| #A0002 | #B00002 |
| #A0002 | #B00003 |
| . . . | . . . |
| #A0002 | #B17904 |
| #A0002 | #B17905 |

In operation S20, the first classification unit 11B classifies respective material component images 3 into any one of the types of available material components using the first trained model 15B stored in the storage unit 15.

As described above, the first trained model 15B is an example of a classification model of the material component images 3 generated by machine learning using training data where material component images of known types are an input and the types of material components in those images are an output. In some implementations, the number of nodes in an output layer of the first trained model 15B is the number of the types of material components that can be classified by the first processing device 10, and the nodes of the output layer of the first trained model 15B are associated with the types of material components, respectively, on a one-to-one basis.

When a material component image 3 is input to the first trained model 15B, the first trained model 15B according to this example outputs the degree of suitability from each of the nodes in the output layer. Because each of the nodes in the output layer is associated with a respective type of material component, the first classification unit 11B classifies the type of material component associated with the node of the output layer of the first trained model 15B that has the highest degree of suitability with the material component image 3 that was input to the first trained model 15B. As such, by (e.g., sequentially) inputting all the material component images 3 extracted from a sample image to the first trained model 15B, the first classification unit 11B classifies the material component images 3 in the sample image into the various types of material components.

The first classification unit 11B associates the types of material components in the material component images 3 that are classified using the first trained model 15B with the material component image IDs in a classification list. Table 2 shows an example of a classification list, which includes the types of material components. The values in the classification field of the classification list of Table 2 do not need to be material component names and may be reference numerals representing respective material component names. The classification list where the types of material components are associated with respective material component image IDs is an example of the classification result of the material component images. While referred to as a classification list in this example, the classification information is not limited to any particular arrangement. For example, shown here as a table for ease of explanation, the classification information may be stored in any suitable arrangement.

TABLE 2

| Sample ID | Material Component Image ID | Classification |
|---|---|---|
| #A0002 | #B00001 | Red Blood Cell |
| #A0002 | #B00002 | White Blood Cell |
| #A0002 | #B00003 | Other Material Component |
| ... | ... | ... |
| #A0002 | #B17904 | Squamous Epidermal Cell |
| #A0002 | #B17905 | Bacteria |

In operation S30 of FIG. 6, the calculation unit 11C calculates the concentration of a material component in the sample using the classified material component images according to the classification list obtained by the process of operation S20. The concentration may be any measure of the quantity of respective material components in the sample, such as volume, weight, mass, etc.

In this example, the concentration is a number concentration of the material component that refers to an index representing a cardinality (or number) of the material component in a predetermined unit volume such as 1 μL. The calculation unit 11C calculates the number concentration of each of the material components in the sample using a concentration arithmetic expression stored in advance (e.g., in the storage unit 15). Table 3 shows an example of the concentration arithmetic expression for each of the material components.

TABLE 3

| Classification | Number of Images | Concentration Arithmetic Expression | Number Concentration [Pieces/μL] |
|---|---|---|---|
| Red Blood Cell | X1 | y = a1*x + b1 | Y1 |
| White Blood Cell | X2 | y = a2*x + b2 | Y2 |
| Non-Squamous Epidermal Cell | X3 | y = a3*x + b3 | Y3 |
| Squamous Epidermal Cell | X4 | y = a4*x + b4 | Y4 |
| Other Cast | X5 | y = a5*x + b5 | Y5 |
| Bacteria | X6 | y = a6*x + b6 | Y6 |
| Crystal | X7 | y = a7*x + b7 | Y7 |
| Yeast | X8 | y = a8*x + b8 | Y8 |
| Hyaline Cast | X9 | y = a9*x + b9 | Y9 |
| Mucus | X10 | y = a10*x + b10 | Y10 |
| Spermatozoa | X11 | y = a11*x + b11 | Y11 |
| White Blood Cell Clump | X12 | y = a12*x + b12 | Y12 |
| Other Material Component | X13 | y = a13*x + b13 | Y13 |

In the concentration arithmetic expressions shown in Table 3, the operator "*" represents the multiplication operation. The number concentration y of a type of material component is represented by, for example, a linear function of a variable x that is the number of the material component images 3 classified with the type of material component. In the concentration arithmetic expressions, a1, a2, . . . , aN represents a slope determined for a respective type of material component, and b1, b2, . . . , bN represents an intercept determined for the respective type of material component. N represents the number of different material components that may be present in the sample, which is based on the type of sample. Accordingly, X1, X2, . . . , XN represents the number (or cardinality) of material component images 3 in each of the N types of material components, and Y1, Y2, . . . , YN represents the number concentration for each of the N types of material components. The concentration arithmetic expression for each of the material components is an arithmetic expression that is determined in advance by experimentation or a computer simulation that identifies a relationship between a number of material component images where the material component is imaged in a sample having a predetermined volume and the number concentration of the material component. Each concentration arithmetic expression (equation, formula, etc.) may be stored in the first processing device (e.g., the storage unit 15).

The concentration arithmetic expression shown in Table 3 is merely an example, and the concentration arithmetic expression for each of the material components is not limited to a linear function. Table 3 shows the concentration arithmetic expressions corresponding to 13 types of material components, but the number of classifications for the material components of a sample by the first processing device 10 is merely an example.

In operation S40 of FIG. 6, the control unit 10A refers to the concentration of a type of the material component calculated by the calculation unit 11C in operation S30 and determines whether recalculation of the concentration is recommended. This determination may be done by comparing the concentration or a value derived from the concentration to some type of review condition. If the review condition is satisfied, recalculation is not needed.

In some implementations, the determination in operation S40 is performed by determining whether an item regarding a test of the sample (hereinafter referred to as a determination item) satisfies a review condition. The review condition is a condition that is set by the user through the operation unit 17 that indicates when recalculation of the concentration is recommended. The determination item and the review condition may be defined in advance and stored in, for example, the storage unit 15. The determination item and the review condition may be defined or modified by the user through the operation unit 17. Details of the determination item and the review condition will be described below.

When the review condition is not satisfied at operation S40, the recalculation of the concentration of a material component is not necessary. The process advances to operation S50.

In operation S50, the output unit 11F displays the measurement status of the concentration of the material component in the sample on the display unit 16. Hereinafter, this measurement status may be referred to as the measurement status of the material component concentration or the measurement status of the urinary material component concentration to conform with the example herein.

Here, a screen on which the output unit 11F causes the display unit 16 to display will be described. The screen that is displayed on the display unit 16 by the output unit 11F includes, for example, a status screen 61, a work list screen 62, a dashboard screen 63, an atlas screen 64, or some combination thereof.

Figure 8:
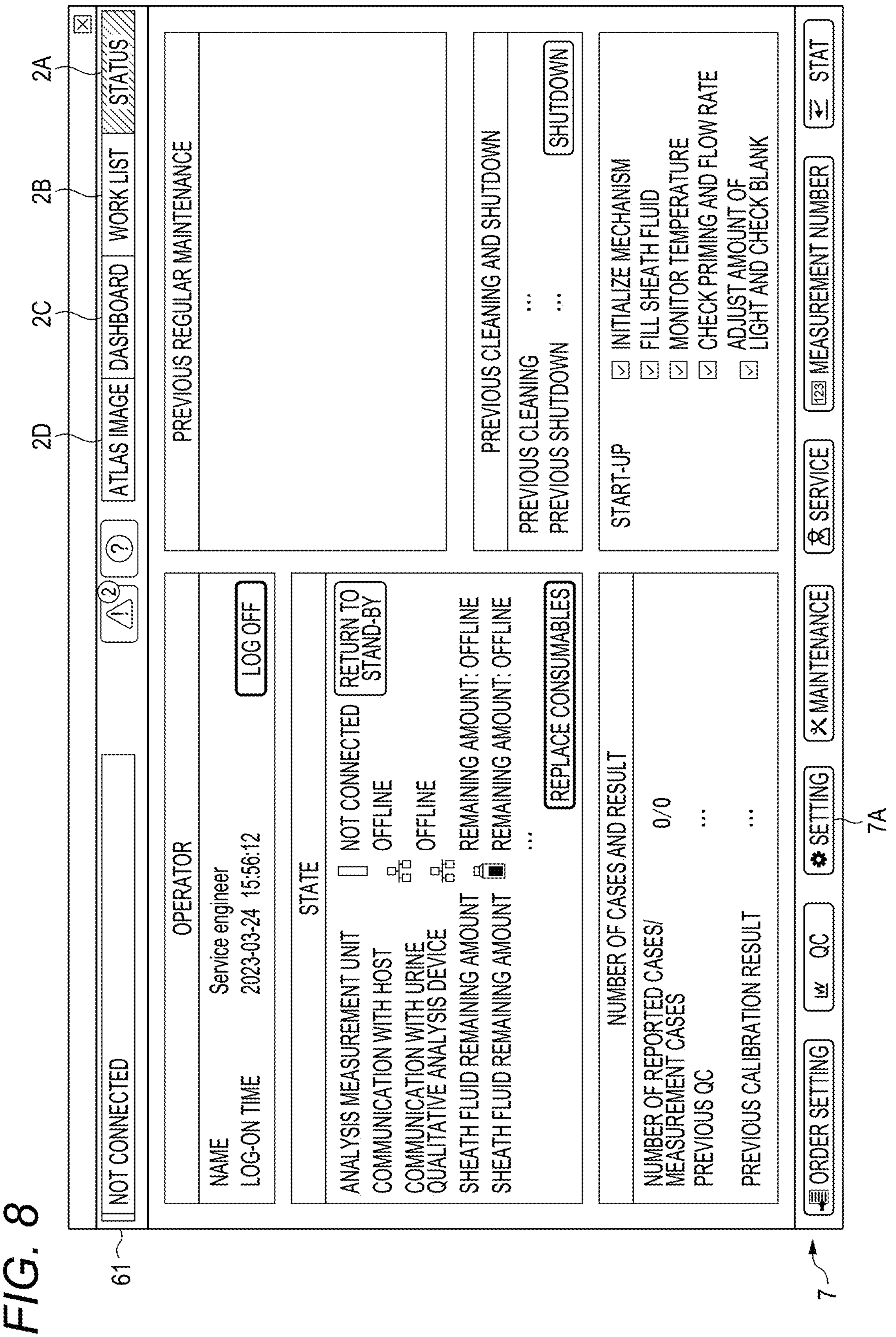
FIG. 8 is a diagram illustrating an example of a status screen.
Figure 9:
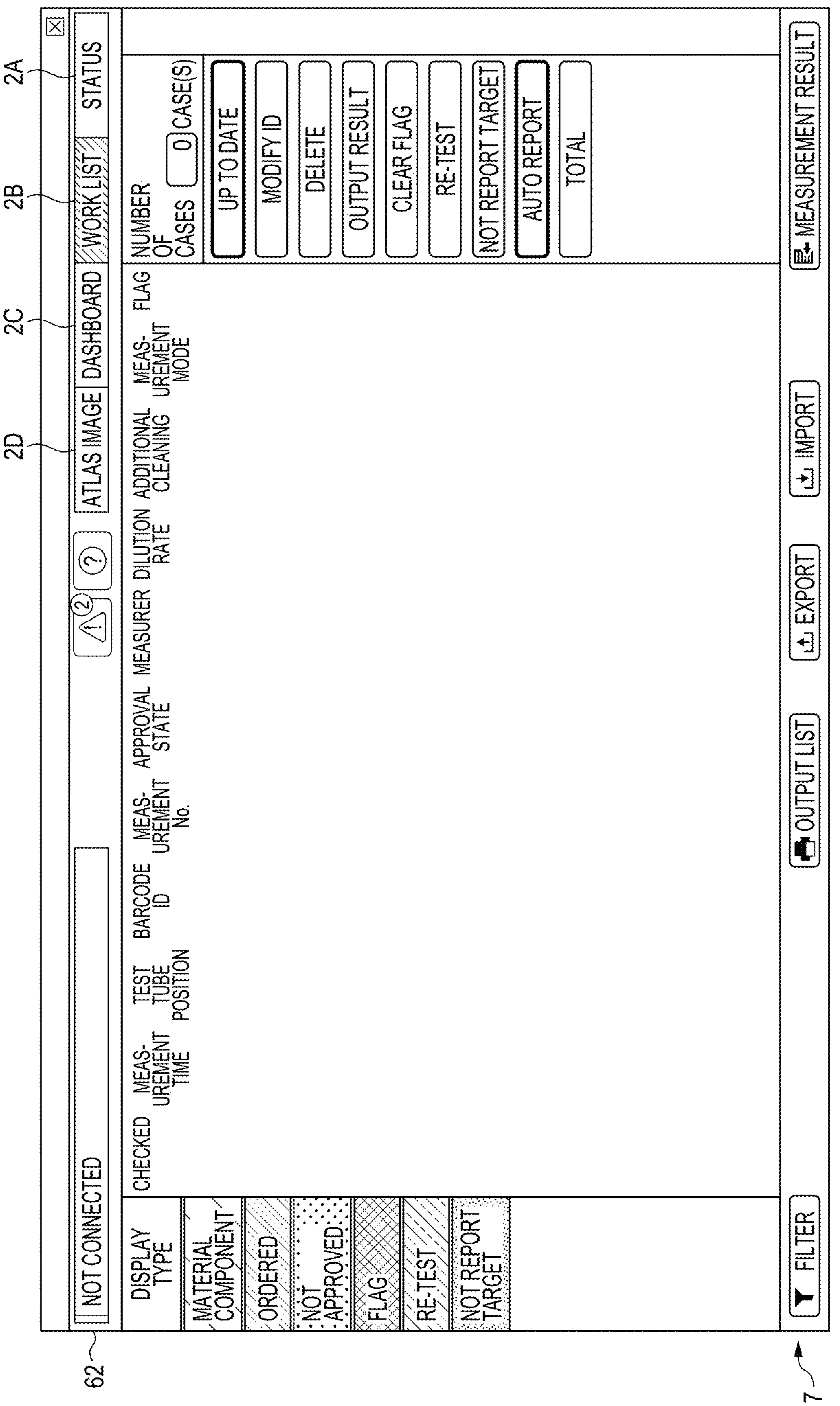
FIG. 9 is a diagram illustrating an example of a work list screen.
Figure 10:
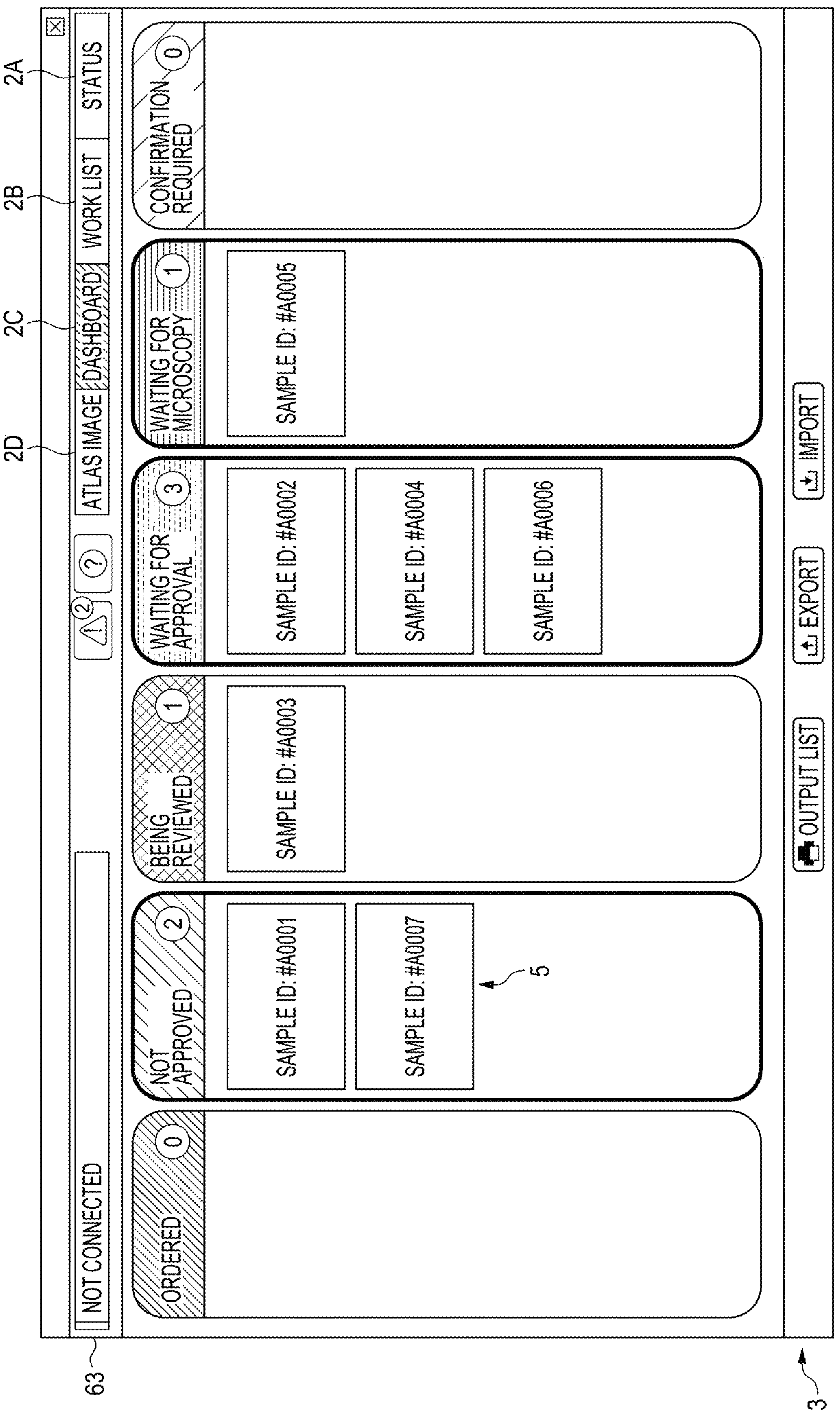
FIG. 10 is a diagram illustrating an example of a dashboard screen.
Figure 11:
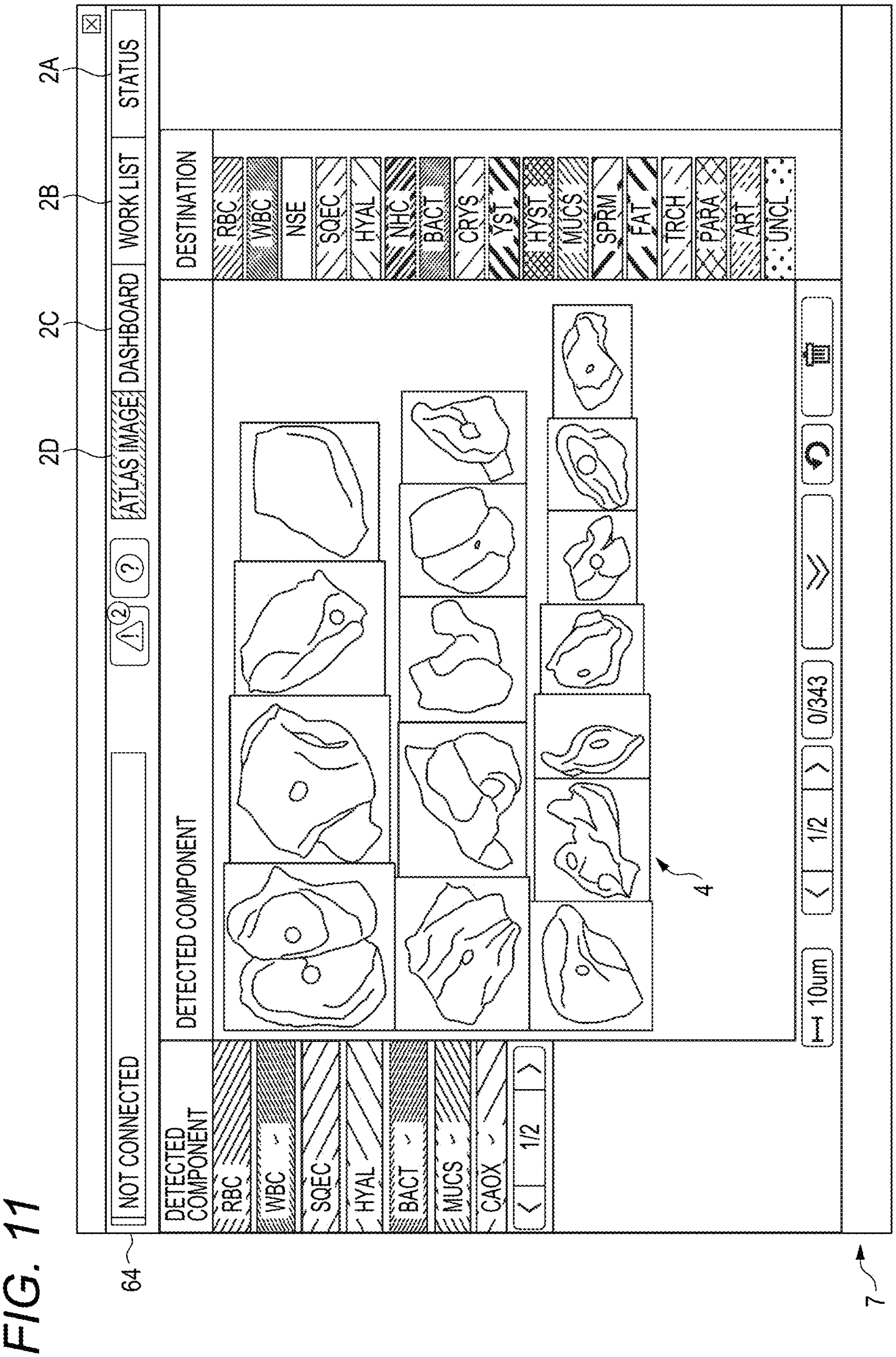
FIG. 11 is a diagram illustrating an example of an atlas screen.

FIG. 8 is a diagram illustrating an example of the status screen 61. FIG. 9 is a diagram illustrating an example of the work list screen 62. FIG. 10 is a diagram illustrating an example of the dashboard screen 63. FIG. 11 is a diagram illustrating an example of the atlas screen 64.

When the user selects a status button 2A, the output unit 11F displays the status screen 61 on the display unit 16. When the user selects a work list button 2B, the output unit 11F displays the work list screen 62 on the display unit 16. When the user selects a dashboard button 2C, the output unit 11F displays the dashboard screen 63 on the display unit 16. When the user selects an atlas image button 2D, the output unit 11F displays the atlas screen 64 on the display unit 16. The selection may be made by any means, such as using a mouse, a stylus, or the like.

The status screen 61 can display information regarding the user who operates the first processing device 10, that is, an operator. The status screen 61 can display the connection status of the first processing device 10 to another device. The status screen 61 can display the state of the first processing device 10 such as a remaining amount of consumables used for the measurement of the sample, a number of measurement cases of the sample, a calibration result of the first processing device 10, or some combination thereof. The status screen 61 can display information regarding previous regular maintenance, information regarding the cleaning state of a member required to be cleaned such as the supply tube 80 and the like, a shutdown of the first processing device 10, information regarding a start-up process at the time of start of the first processing device 10, or some combination thereof. The described displays may be separately displayed on the status screen 61, or two or more of the described displays may be displayed together on the status screen 61.

The work list screen 62 can display complete information regarding the measurement of the sample. For example, the information can include the measurement time (e.g., start time, end time, elapsed time) of the sample for each sample. The work list screen 62 is arranged in the form of a single list in FIG. 9, but any arrangement is possible.

The dashboard screen 63 can display the measurement status of the material component concentration for each sample in any arrangement. In the example shown in FIG. 10, a sample panel 5 is associated with each of the samples. The sample panel 5 displays, for example, the sample ID of the sample associated with the sample panel 5. In the dashboard screen 63 as shown, separate display areas are defined for the different measurement statuses. In this example, the display areas are labeled with respective measurement statuses of Ordered, Not Approved, Being Reviewed, Waiting for Approval, Microscopy, and Confirmation Required. The measurement status of a material component concentration in a sample associated with a sample panel 5 is shown in part by displaying the sample panel 5 within the applicable display area.

The atlas screen 64 displays one or more atlas images 4. An atlas image is a standard component image for a type of material component. That is, the atlas image 4 is an example image for the type of the material component. An atlas image may be obtained from an atlas or library of material component images obtained either externally or from storage, such as the storage unit 15.

In an operation bar 7 disposed in each screen (below the status screen 61, the work list screen 62, the dashboard screen 63, and the atlas screen 64 in these example), various buttons corresponding to the respective screens are displayed.

Referring again to FIG. 6, when the process proceeds to operation S50, the material component concentration is not approved. Therefore, the control unit 10A sets the measurement status of the material component concentration to Not Approved. Accordingly, the output unit 11F displays, on the display unit 16, the dashboard screen 63 with the sample panel 5 corresponding to the sample to be measured in the area labeled Not Approved.

Next, in operation S60, the acceptance unit 11G determines whether selection by the user of any one of the sample panels 5 displayed on the dashboard screen 63 is received. When selection of a sample panel 5 is not received, operation S60 is repeatedly executed until a sample panel 5 is selected. Accordingly, the selection status of a sample panel 5 by the user is monitored. When selection of a sample panel 5 is received, the process proceeds to operation S70.

In operation S70, the control unit 10A determines whether the qualitative test result of the sample associated with the selected sample panel 5 is stored (e.g., in the server 35). In an example, the control unit 10A determines whether the qualitative test result associated with the same sample ID as the sample ID associated with the selected sample panel 5 is stored in the server 35. When the qualitative test result is stored, the process advances to operation S80. For convenience of description, the sample associated with the selected sample panel 5 will be referred to as the selected sample.

In operation S80, the control unit 10A acquires the qualitative test result of the selected sample from the server 35, and the process advances to operation S90.

In the determination process of operation S70, when the control unit 10A determines that the qualitative test result of the selected sample is not stored, the process advances to operation S90 without executing the process of operation S80.

In operation S90, the output unit 11F can display an approval screen 65 on the display unit 16. The approval screen 65 shows that the material component concentration of the selected sample is approved.

When the qualitative test result of the selected sample is acquired by the process of operation S80, the output unit 11F displays the material component concentration of the selected sample and the qualitative test result of the selected sample on the approval screen 65. In contrast, when the qualitative test result of the selected sample is not stored (e.g., in the server 35), the output unit 11F displays only the material component concentration of the selected sample on the approval screen 65.

Figure 12:
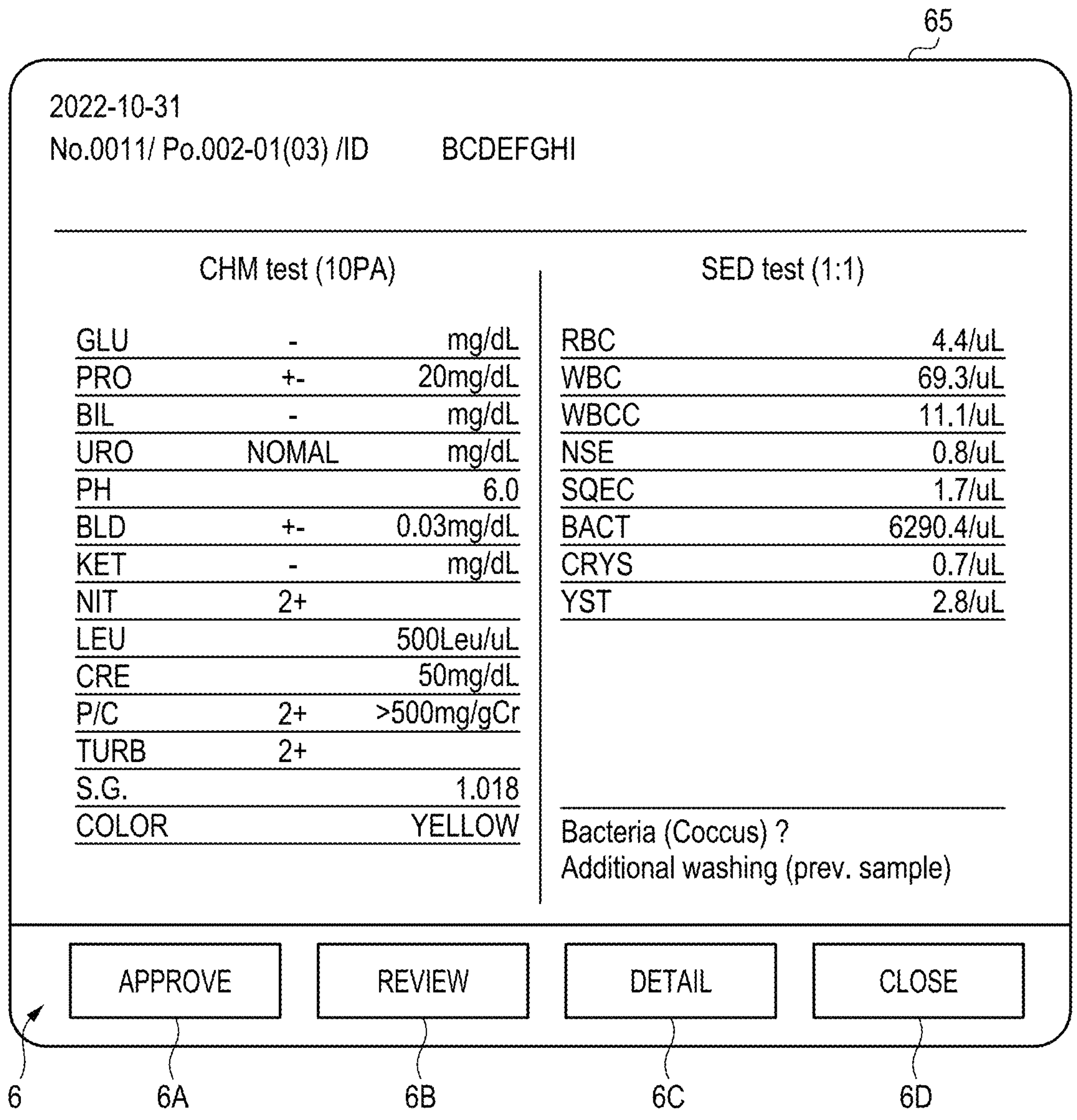
FIG. 12 is a diagram illustrating an example of an approval screen.

FIG. 12 is a diagram illustrating an example of the approval screen 65 on which the material component concentration and the qualitative test result can be displayed. In the approval screen 65 of FIG. 12, the left table displays a urine qualitative test result, and the right table displays a urinary material component concentration. The approval screen 65 may be a pop-up screen superimposed on the dashboard screen 63.

On the approval screen 65, one or more selection buttons 6. In the illustrated example, the selection buttons 6 include an approval button 6A, a review button 6B, a display button 6C, and a close button 6D.

The approval button 6A is a button for approving the material component concentration displayed on the approval screen 65, that is, the measurement result of the material component concentration in the selected sample. By approving the material component concentration, the measurement result of the material component concentration in the selected sample is confirmed.

The review button 6B is a button for recalculating the material component concentration in the selected sample. A user may select the review button 6B when the material component concentration displayed on the approval screen 65 is different from a tendency of the material component concentration estimated from the qualitative test result or the like. A user may select the review button 6B when the user wants to calculate a more precise (more accurate, more detailed) material component concentration.

The display button 6C is a button for displaying the material component images 3 of the selected sample that are used for calculating the material component concentration.

The user may select the display button 6C when the user wants to confirm the material components in the selected sample.

The close button 6D is a button for closing the approval screen 65, which in this example returns the screen of the display unit 16 to the dashboard screen 63.

Returning to FIG. 6, in operation S100, the acceptance unit 11G determines whether an instruction from the user is received by selection of a selection button 6 through the operation unit 17. When an instruction from the user is not received, operation S100 is repeatedly executed until any selection button 6 is selected. Thus, the selection status of the selection button 6 by the user is monitored. When an instruction from the user is received, the acceptance unit 11G notifies the received instruction to the control unit 10A, and the process advances to operation S110.

In operation S110, the control unit 10A determines whether a review instruction was received, which results from selection of the review button 6B. When a review instruction is not received, the process advances to operation S120.

In operation S120, the control unit 10A determines whether a display instruction of the material component images 3 is received, which results from selection of the display button 6C. When a display instruction of the material component images 3 is not received, the process advances to operation S130.

In operation S130, the control unit 10A determines whether an approval instruction is received, which results from selection of the approval button 6A. When an approval instruction is not received, it may be assumed that the user selects the close button 6D. When the close button 6D is selected, a display close instruction is notified. Therefore, according to an instruction from the control unit 10A, the output unit 11F closes the approval screen 65, and the process advances to operation S50. As a result, through the process of operation S50, the dashboard screen 63 is displayed on the display unit 16, and the measurement status of the material component concentration in each of the samples may be displayed.

If instead the control unit 10A determines that an approval instruction is received in the determination process of operation S130, the process advances to operation S140.

Here, it is assumed that the measurement result of the material component concentration in the selected sample is approved by the user. Accordingly, in operation S140, the control unit 10A transmits the measurement result of the material component concentration associated with the sample ID of the selected sample to the server 35 through the transmission unit 11D. As a result, the material component concentration of the sample measured by the material component analysis device 70 is registered in the server 35, and the measurement process illustrated in FIG. 6 ends. As the material component concentration is registered in the server 35, the output unit 11F can deletes the sample panel 5 associated with the sample of which the material component concentration is approved from the dashboard screen 63.

In the foregoing, it is assumed that a display instruction of the material component images 3 is not received in the determination process of operation S120. If instead the control unit 10A determines that a display instruction of the material component images 3 (e.g., an instruction to display the material component images 3) is received in the determination process of operation S120, the process advances to operation S150.

Here, the user may wish to confirm the shapes or sizes of the material components in the selected sample. Accordingly, in operation S150, the output unit 11F displays a material component display screen 66 on the display unit 16.

Figure 13:
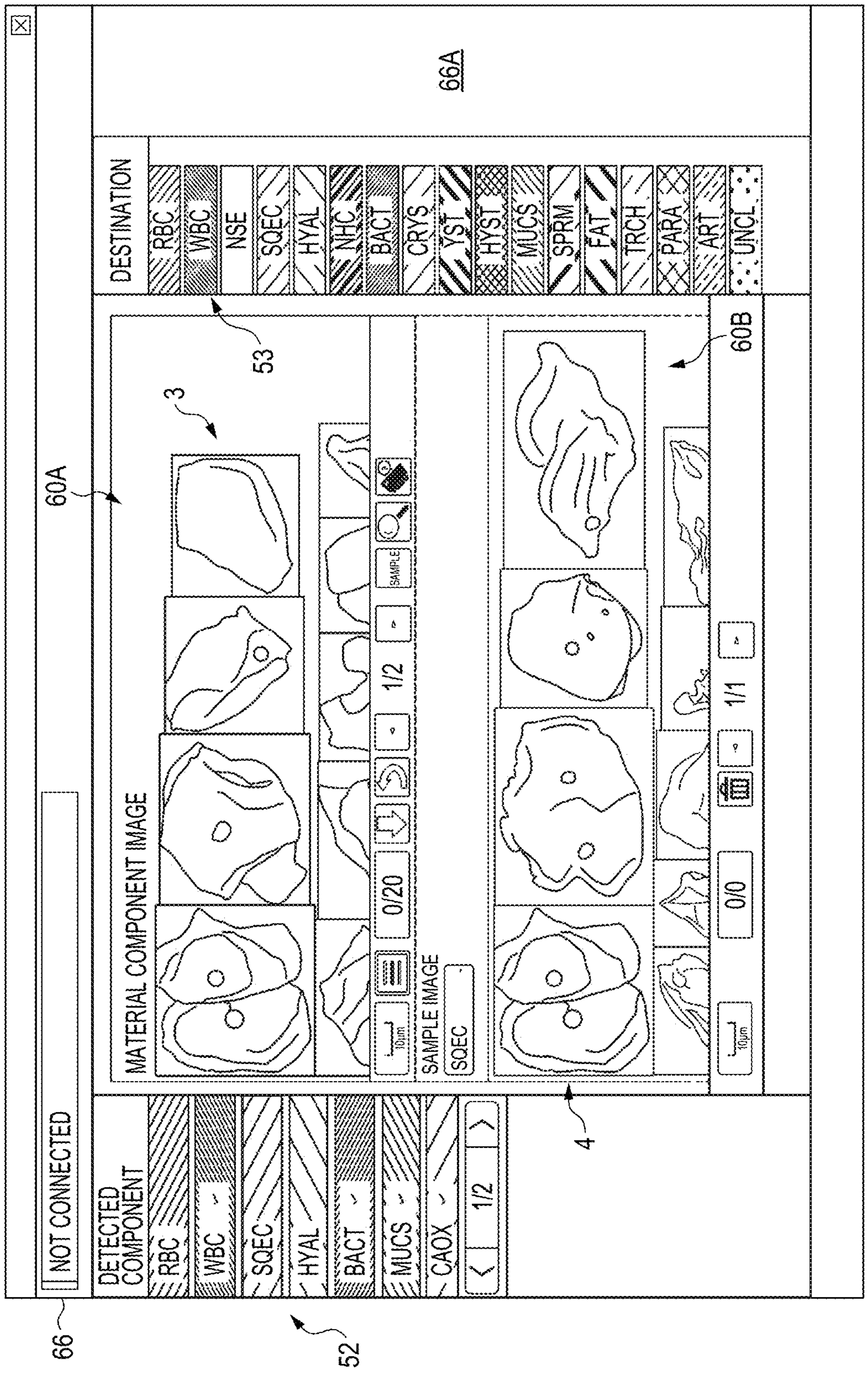
FIG. 13 is a diagram illustrating an example of a material component display screen.

FIG. 13 is a diagram illustrating an example of the material component display screen 66. On the material component display screen 66, the material component images 3 of the material components in the selected sample may be displayed. The material component images 3 of the material components in the selected sample are displayed in a region 60A of the material component display screen 66. Atlas images 4 having the same type(s) of material component as the material component images 3 displayed in the region 60A are displayed in a region 60B of the material component display screen 66. Other arrangements are possible.

In some implementations, the material component display screen 66 includes a first item button group 52. The first item button group 52 includes buttons for the respective types of the material components in the selected sample. In some implementations, the material component display screen 66 includes a second item button group 53. The second item button group 53 includes buttons for each of the types of all the material components that can be classified in the first processing device 10.

The output unit 11F can display, in the region 60A, the material component images 3 of the type of material component associated with the button selected by the user in the first item button group 52. When any button in the second item button group 53 is selected, the output unit 11F can display a reclassification operation screen on the display unit 16. The reclassification operation screen provides an interface for reclassifying a material component image 3 that is selected from the material component images 3 displayed in the region 60A into the type of material component corresponding to any button selected from the second item button group 53.

The output unit 11F may display the qualitative test result of the selected sample in a region 66A of the material component display screen 66. In some implementations, when the urinary sediment measurement result of the selected sample is stored in the server 35, the control unit 10A may acquire the urinary sediment measurement result of the selected sample from the server 35, and the output unit 11F may display the urinary sediment measurement result acquired by the control unit 10A together with a urine qualitative test result in the region 66A.

Returning to FIG. 6, the acceptance unit 11G, in operation S160, determines whether a display close instruction of the material component display screen 66 is received. When a display close instruction is not received, operation S160 is repeatedly executed until the display close instruction is received. Thus, whether a display close instruction is given is monitored. When a display close instruction is received, the process returns to operation S50. Through operation S50, the dashboard screen 63 is displayed on the display unit 16, and the measurement status of the material component concentration in each of the samples may be displayed as described in detail above.

The foregoing describes a sequence of operations that occur when the control unit 10A determines that a review instruction is not received in response to the determination in operation S110. In contrast, when the control unit 10A determines that the review instruction is received, the process advances to operation S180.

Here, the user wants to recalculate the material component concentration in a selected sample. Accordingly, in operation S180, the control unit 10A transmits the material component images 3 obtained from the selected sample together with the sample ID to the second processing device 20 through the transmission unit 11D. The control unit 10A may also transmit information other than the sample ID and the material component images 3 to the second processing device 20 according to an instruction from the user. For example, the control unit 10A may transmit the sample ID and the material component images 3 of the selected sample, the classification list where the types of material components are associated with the material component images 3 in the selected sample (such as Table 2), and the material component concentration for each type of the material component in the selected sample to the second processing device 20.

The material component images 3 that are transmitted to the second processing device 20 by the control unit 10A are preferably all the material component images 3 obtained from the selected sample, but only a portion of the obtained material component images 3 may be transmitted. The user can select the material component images 3 to be transmitted to the second processing device 20.

When the qualitative test result of the selected sample can be acquired from the server 35, the control unit 10A may also transmit the qualitative test result of the selected sample to the second processing device 20.

In this way, the request of the reclassification of the material component images 3 for the second processing device 20 is completed. The operation of transmitting the material component images 3 to the second processing device 20 to allow the second processing device 20 to reclassify the material component images 3 will be referred to as a review. Therefore, in operation S190, the control unit 10A sets the measurement status of the material component concentration of the selected sample to "Being Reviewed". The measurement status of the material component concentration in each of the samples is managed by a measurement status list. The measurement status list is, for example, a list stored in the storage unit 15. Table 4 shows an non-limiting example of the measurement status list.

TABLE 4

| Sample ID | Measurement Status |
|---|---|
| #A0001 | Not Approved |
| #A0002 | Being Reviewed |
| #A0003 | Not Approved |
| . . . | . . . |
| #A0016 | Waiting for Approval |

In the example of the measurement status list shown in Table 4, the measurement status of the material component concentration is set for each of 16 samples represented by Sample IDs #A0001 through #A0016.

According to the setting of the measurement status of the material component concentration, the output unit 11F can display, on the display unit 16, a dashboard screen like the dashboard screen 63 illustrated in FIG. 10. A sample panel 5 associated with the selected sample may be included in the display area that matches the measurement status of the material component concentration. Here, as the measurement status of the material component concentration is "Being Reviewed", the sample panel 5 associated with the selected sample is displayed in the Being Reviewed area of the dashboard screen 63. Then, the measurement process illustrated in FIG. 6 ends.

The foregoing sequence of operations is performed when the control unit 10A determines that the determination item does not satisfy the review condition in operation S40 of FIG. 6. On the other hand, when the control unit 10A determines that the determination item satisfies the review condition in operation S40, the process advances to operation S170.

Here, the control unit 10A determines that recalculation of the material component concentration is necessary.

In operation S170, the control unit 10A determines whether an automatic transmission setting to the second processing device 20 is on. When the automatic transmission setting is off, the control unit 10A cannot transmit the material component images 3 obtained from the sample to the second processing device 20 and cannot request reclassification of the material component images 3 without permission of the user. Therefore, the process advances to operation S50. That is, the control unit 10A displays the dashboard screen 63 on the display unit 16 and entrusts the determination of whether recalculation of the material component concentration is necessary to the user. The control unit 10A can set the measurement status of the material component concentration of the sample to "Waiting for Approval" and display the sample panel 5 of the sample in the Waiting for Approval area of the dashboard screen 63.

In contrast, where the automatic transmission setting is on, the process advances to operation S180. As described above, in operation S180, the control unit 10A transmits the material component images 3 obtained from the sample to be measured to the second processing device 20 through the transmission unit 11D. Accordingly, when the review condition in the determination item is satisfied, the material component images 3 of the sample are automatically transmitted from the first processing device 10 to the second processing device 20 without the user instruction. Whether to allow automatic transmission can be set by the user.

Reclassification of Material Component Images

Figure 14:
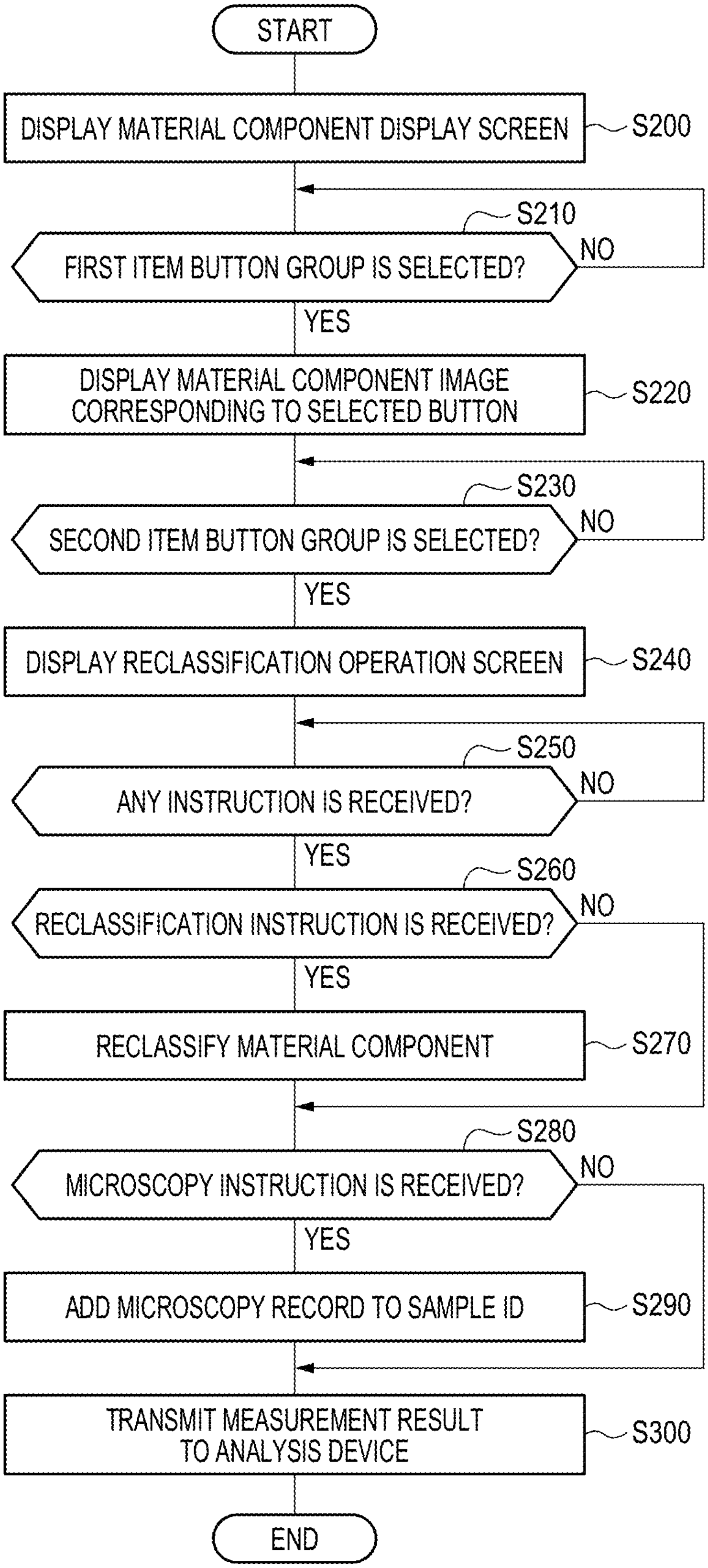
FIG. 14 is a flowchart diagram illustrating an example of a reclassification process of the second processing device.

Next, the operations of the second processing device 20 will be described. FIG. 14 is a flowchart illustrating an example of the reclassification process that is executed by the second processing device 20 when the material component images 3 of the sample represented by the sample ID are received from the first processing device 10. The CPU 21 of the second processing device 20 reads the processing program 25A stored in the storage unit 25 and executes the reclassification process. Hereinafter, an example is described where the second processing device 20 receives the material component images 3 and the classification list of the sample represented by the sample ID, that is, the classification result by the classification unit 11B from the first processing device 10.

For example, a specialized laboratory technician who checks the material component images 3 and determines the types of material components in the material component images 3 can operate the second processing device 20 to reclassify the material component images 3.

First, in operation S200, the display control unit 21C can display a material component display screen on the display unit 26. The material content display screen can be similar to the material content display screen 66 shown by example in FIG. 13. On the material component display screen 66, the material component images 3 received from the first processing device 10 may be displayed based on the classifications of the classification list that are also received from the first processing device 10.

In operation S210, the control unit 20A determines whether any button of the first item button group 52 in the material component display screen 66 is selected through the operation unit 27. When no button of the first item button group 52 is selected, operation S210 is repeatedly executed until any button of the first item button group 52 is selected.

Thus, the selection status of the first item button group 52 by the laboratory technician is monitored. When any button of the first item button group 52 is selected, the process advances to operation S220.

In operation S220, the display control unit 21C displays the material component images 3 of the type of material component associated with the selected button in the region 60A of the material component display screen 66.

In operation S230, the control unit 20A determines whether any button of the second item button group 53 in the material component display screen 66 is selected through the operation unit 27. When no button of the second item button group 53 is selected, operation S230 is repeatedly executed until any button of the second item button group 53 is selected. Thus, the selection status of the second item button group 53 by the laboratory technician is monitored. When any button of the second item button group 53 is selected, the process advances to operation S240.

In operation S240, the display control unit 21C displays a reclassification operation screen on the display unit 26. Through the reclassification operation screen, the laboratory technician can reclassify any of the material component images 3 for which an error was recognized in the classification process of the first processing device 10. When the qualitative test result of the sample is transmitted from the first processing device 10, the laboratory technician may refer to the qualitative test result to reclassify the material component images 3.

In operation S250, the control unit 20A determines whether any instruction is received from the laboratory technician. When no instruction is received, operation S250 is repeatedly executed until any instruction is received. Thus, the control unit 20A waits until an instruction is received from the laboratory technician. On the other hand, when any instruction is received, the process advances to operation S260.

Next, in operation S260, the control unit 20A determines whether a reclassification instruction is received from the laboratory technician. When the reclassification instruction is received, the process advances to operation S270.

In operation S270, a reclassification unit, such as the second classification unit 21B described previously, reclassifies the type of material components in one or more material component image 3 selected by the laboratory technician into the type designated by the laboratory technician, and the process advances to operation S280. Specifically, the control unit 20A updates the classification field of the classification list received by the second processing device 20. Table 5 shows an example of the classification list where the material component image 3 represented by the material component image ID #B00001 is reclassified from red blood cell to yeast with respect to the classification list shown Table 2. The updated classification list is an example of the reclassification result of the material component images 3 by the second classification unit 21B.

TABLE 5

| Sample ID | Material Component Image ID | Classification |
|---|---|---|
| #A0002 | #B00001 | Yeast |
| #A0002 | #B00002 | White Blood Cell |
| #A0002 | #B00003 | Other Material Component |
| . . . | . . . | . . . |
| #A0002 | #B17904 | Squamous Epidermal Cell |
| #A0002 | #B17905 | Bacteria |

When the classification list is not received from the first processing device 10, the control unit 20A may generate a classification list where the type of material component in a respective material component image 3 selected by the laboratory technician is associated with the material component image IDs.

Returning to operation S260, when a reclassification instruction is not received in operation S260, the process advances to operation S280 without executing operation S270.

In operation S280, the control unit 20A determines whether a microscopy instruction is received from the laboratory technician. A microscopy instruction refers to an instruction to require the sample to be examined in detail, for example, using a microscopy method of testing the types or the number of the material components in the sample by visual inspection of a person with a laboratory microscope or the like. When a microscopy instruction is received, the process advances to operation S290.

In operation S290, the control unit 20A adds a microscopy status to the sample ID to represent that a microscopy instruction was received from the laboratory technician, and the process advances to operation S300. When a microscopy instruction is not received in operation S280, the process advances to operation S300 without executing operation S290.

In operation S300, the control unit 20A returns the classification list on which the sample ID and the reclassification result(s) are reflected to the first processing device 10 through the return unit 21D. The classification list returned to the first processing device 10 may omit those material component images 3 not reclassified, or the classification list can include all material component images 3 of the selected sample. When a microscopy instruction is received, the microscopy status may be added to the sample ID that is returned to the first processing device 10. The reclassification process illustrated in FIG. 14 then ends.

The example in which the material component images 3 are reclassified according to reclassification instructions from a laboratory technician has been described above. However, the second processing device 20 may reclassify the material component images 3 without reclassification instructions from a laboratory technician. The second classification unit 21B may reclassify one or more material component images 3 (e.g., designated by the laboratory technician) using the second trained model 25B that is stored in advance in the storage unit 25.

As described above, the second trained model 25B is a classification model having better classification performance than the first trained model 15B. Accordingly, the second trained model 25B classifies the material component images 3 more accurately than the first trained model 15B, and thus can correct an error in the classification of a material component image 3 made using the first trained model 15B.

The control unit 20A can reclassify only some of the material component images 3 (e.g., as designated by a laboratory technician). In some implementations, when the second trained model 25B is used, the control unit 20A reclassifies all the material component images 3 received from the first processing device 10 into the available types of material components without further input.

Remeasurement of Material Component Concentration

Next, operations of the first processing device 10 upon receipt of the classification list from the second processing device 20 will be described.

Figure 15:
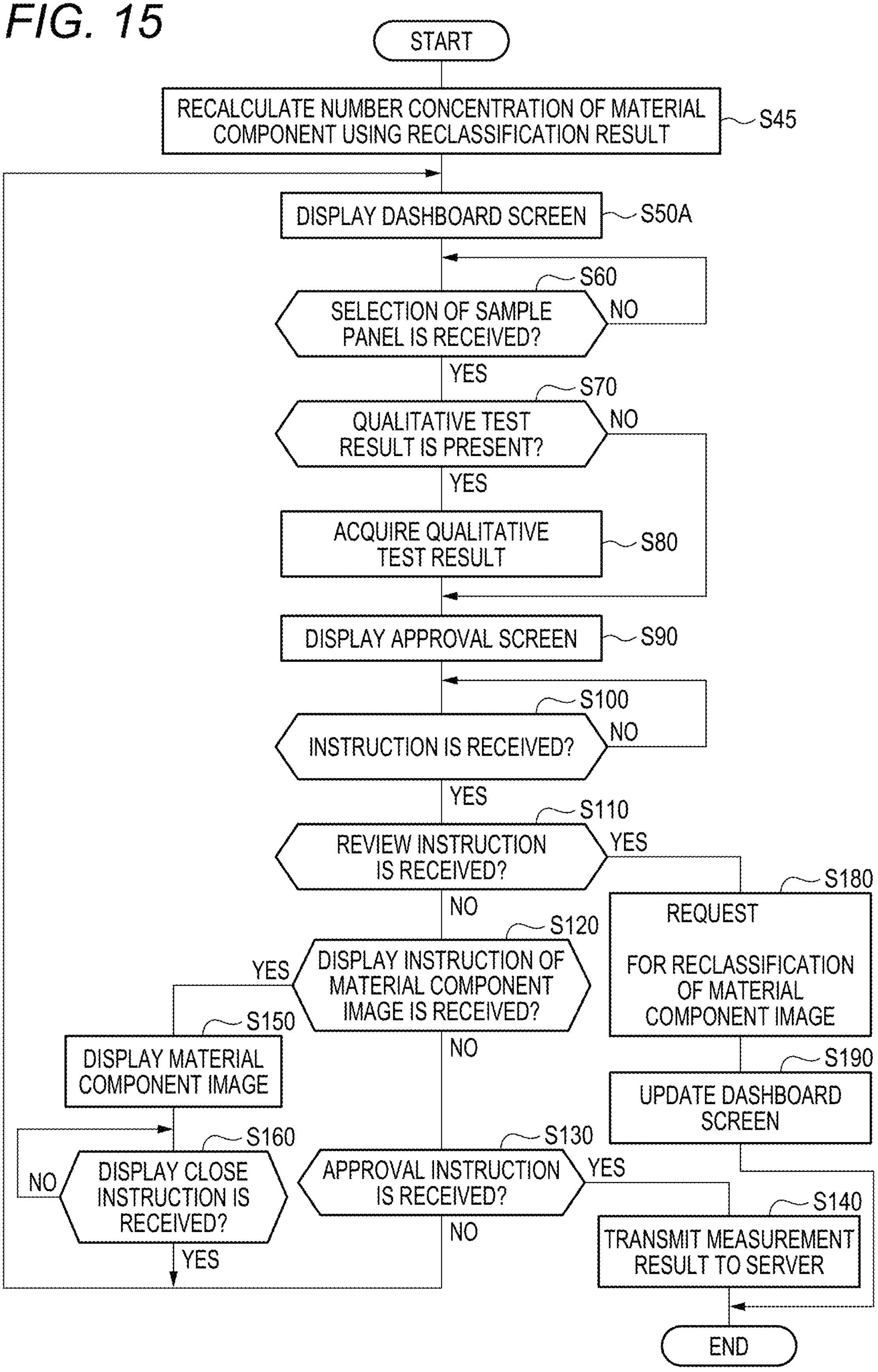
FIG. 15 is a flowchart diagram illustrating an example of a remeasurement process of the first processing device.

FIG. 15 is a flowchart illustrating an example of the remeasurement process executed by the first processing device 10 when the classification list is received from the second processing device 20. The CPU 11 of the first processing device 10 reads the processing program 15A stored in the storage unit 15 and executes the remeasurement process.

The flowchart illustrated in FIG. 15 is different from the flowchart of the measurement process illustrated in FIG. 6. In particular, in FIG. 15, operation S10 to operation S40 and operation S170 from FIG. 6 are not included, and operation S45 is added. Operation S50 of FIG. 6 is replaced with the process of operation S50A in FIG. 15. Because the other processes are the same as those of FIG. 6, repetitive description will be omitted when explaining the remeasurement process of the first processing device 10.

When the classification list in which the sample ID and the reclassification result of the material component images 3 are reflected is received from the second processing device 20, operation S45 is executed.

In operation S45, the calculation unit 11C refers to the classification list received from the second processing device 20 to recalculate the material component concentration for each type of material component within the sample. In the example herein, this recalculation is performed by calculating the number of material component images 3 for each type of material component and substitutes the recalculated number(s) into the concentration arithmetic expression shown in Table 3. The output is the material component concentration for each type of material component.

In operation S50A, the control unit 10A refers to the sample ID received from the second processing device 20, and when a microscopy status is associated with the sample ID, the control unit 10A sets the measurement status of the material component concentration in the sample represented by the sample ID to "Waiting for Microscopy". For example, the status may be updated in the measurement status list shown in Table 4. When a microscopy status is not associated with the sample ID, the control unit 10A may set the measurement status of the material component concentration in the sample represented by the sample ID to "Waiting for Approval", e.g., in the measurement status list shown in Table 4.

The output unit 11F can display, on the display unit 16, the dashboard screen 63 where the sample panel 5 associated with respective samples is displayed in the display area that matches the measurement status of the material component concentration set in the measurement status list. Accordingly, the display position of the sample panel 5 in the dashboard screen 63 is updated according to the latest measurement status of the material component concentration.

Next, the user can select any sample panel 5 from the updated dashboard screen 63 to execute the processes in and after operation S60 described above. That is, for the sample corresponding to the selected sample panel 5, the approval of the measurement result of the material component concentration, the review of the measurement result of the material component concentration, the display of the material component images 3, and the like, may be repeatedly executed. The remeasurement process illustrated in FIG. 15 ends after operation S140 or operation S190.

Review Condition

Hereinabove, the measurement of the material component concentration in the material component processing system 100 has been described. In particular, in operation S40 of FIG. 6, the control unit 10A of the first processing device 10 determines whether the determination item satisfies the review condition. Hereinafter, examples of the determination item and the review condition to which the control unit 10A refers in operation S40 of FIG. 6 will be described in detail with initial reference to a setting screen for setting operations of various functions in a material component analysis device, such as the urinary material component analysis device 70.

Referring back to FIG. 8, when a setting button 7A in the operation bar 7 of the status screen 61 is selected by the user, the output unit 11F displays a setting screen 55 on the display unit 16.

Figure 16:
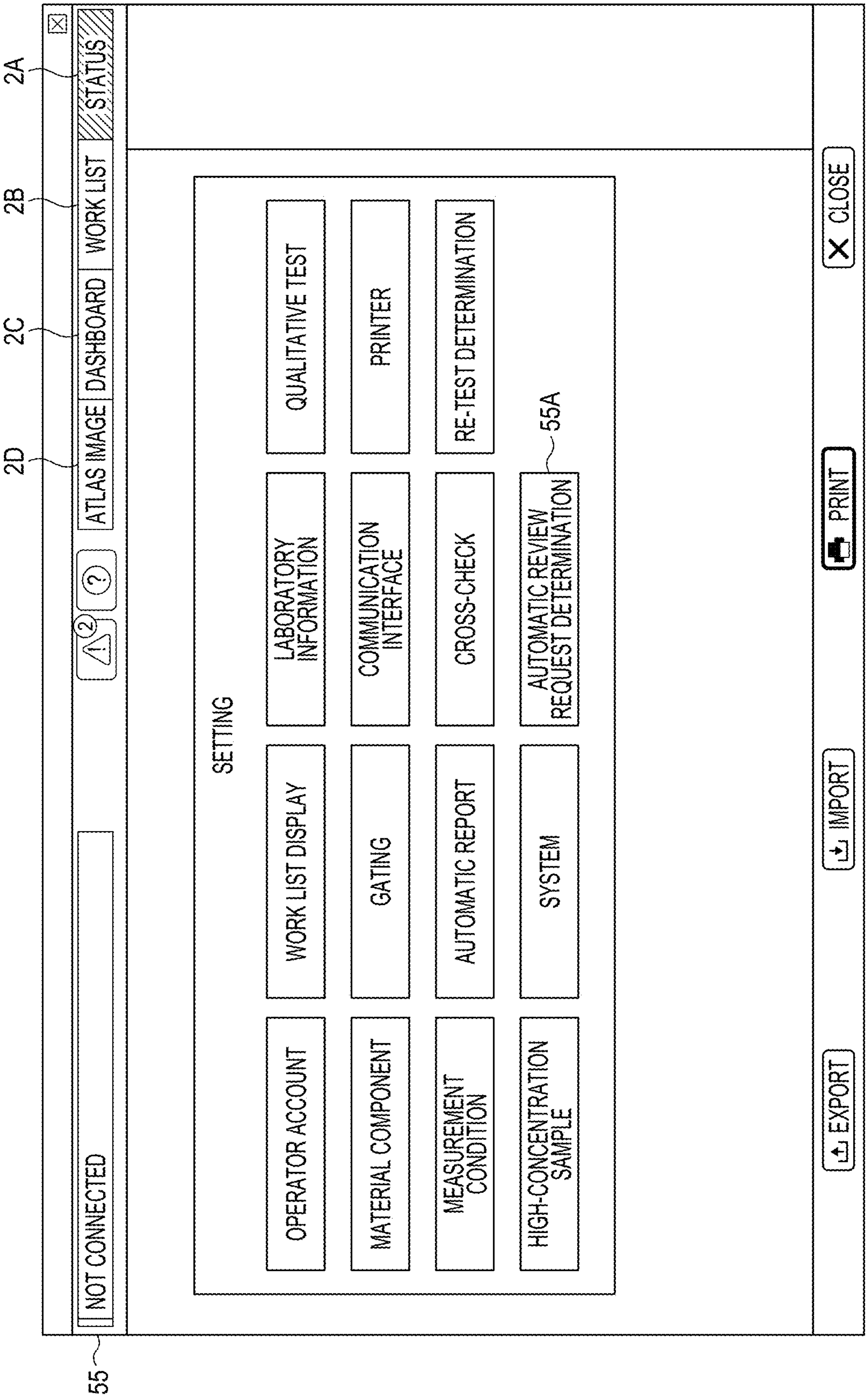
FIG. 16 is a diagram illustrating an example of a setting screen.

FIG. 16 is a diagram illustrating an example of the setting screen 55. The setting screen 55 can include an operator account button for registering the user in and deleting the user from the first processing device 10. When an automatic review request determination button 55A on the setting screen 55 is selected by the user, the output unit 11F displays an automatic review request determination screen 56 on the display unit 16.

Figure 17:
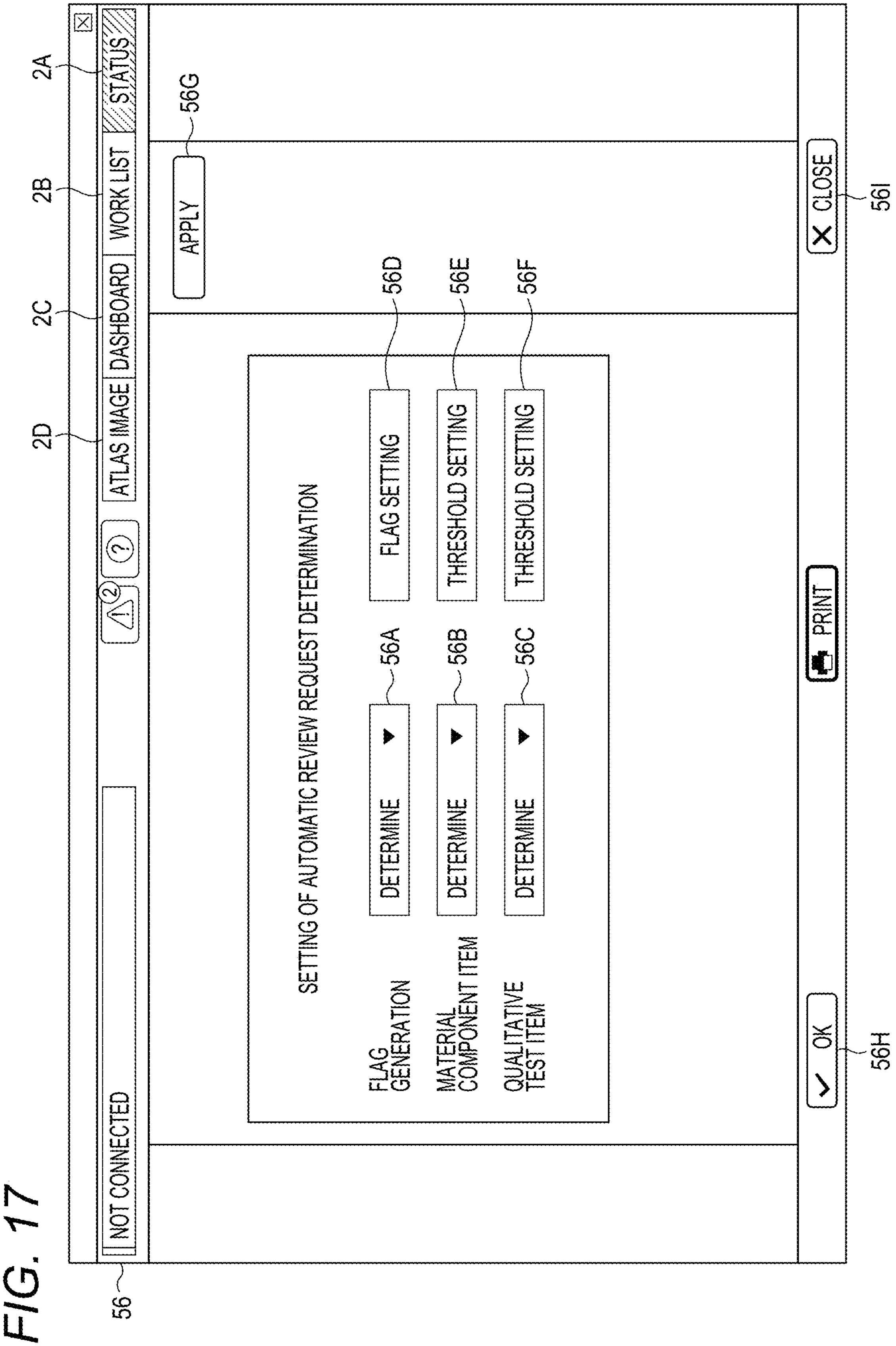
FIG. 17 is a diagram illustrating an example of an automatic review request determination screen.

FIG. 17 is a diagram illustrating an example of the automatic review request determination screen 56. The automatic review request determination screen 56 is a screen for selecting the type of the determination item to which the control unit 10A refers to execute an automatic review request. The automatic review request is a review request that is executed by the determination of the first processing device 10 that the determination item satisfies the review condition at operation S170 regardless of the intention of the user.

As illustrated in FIG. 17, examples of the types of determination items include a flag, a material component item, a qualitative test item, or any combination thereof.

The flag refers to an event to be monitored that can occur in the process of testing the sample. The occurrence status of the event may be represented by flags respectively identified as Occurred and Not Occurred. That is, a flag can be generated when an event has occurred that should not have occurred, or a flag can be generated when an event has not occurred that should have occurred. In either case, the occurrence of the event to be monitored will be referred to as "flag generated".

The material component item refers to the type of the material component that can be analyzed in the material component analysis device, such as the urinary material component analysis device 70.

The qualitative test item refers to each of the items of the qualitative tests that can be analyzed in the qualitative analysis device, such as in the urine qualitative analysis device 30.

In the determination items, pulldown menus 56A, 56B, and 56C are provided for setting whether to use the corresponding determination item as a determination target of the review condition. Each of the pulldown menus 56A, 56B, and 56C may include an option "Determine" for setting the corresponding determination item as a determination target of the review condition and an option "Not Determine" for omitting the corresponding determination item from any review or determination related to automatic transmission. The user sets the options of the pulldown menus 56A, 56B, and 56C through the operation unit 17. In the example of the automatic review request determination screen 56 illustrated in FIG. 17, all the determination items including the flag, the material component item, and the qualitative test item are set to determination targets of the review condition, but this is not necessary. No determination items may be used, only one determination item may be used, or any combination of determination items may be used.

In the automatic review request determination screen 56, a setting button for setting the review condition of the determination item is provided for each of the types of the determination items. A flag setting button 56D is a setting button for setting the review condition of the flag. A threshold setting button 56E is a setting button for setting the review condition of the material component item. A threshold setting button 56F is a setting button for setting the review condition of the qualitative test item.

The user generates the review condition through a review condition setting screen 57 that is displayed on the display unit 16 when selecting the setting button corresponding to the determination item for which the review condition is determined. After the generation of the review condition, the user selects an apply button 56G and then selects a save button 56H. The control unit 10A updates the review condition by selecting the apply button 56G, and the control unit 10A stores the updated review condition in the storage unit 15 by selecting the save button 56H.

When a close button 56I is selected by the user, the output unit 11F closes the automatic review request determination screen 56 and may display the setting screen 55 on the display unit 16.

Figure 18:
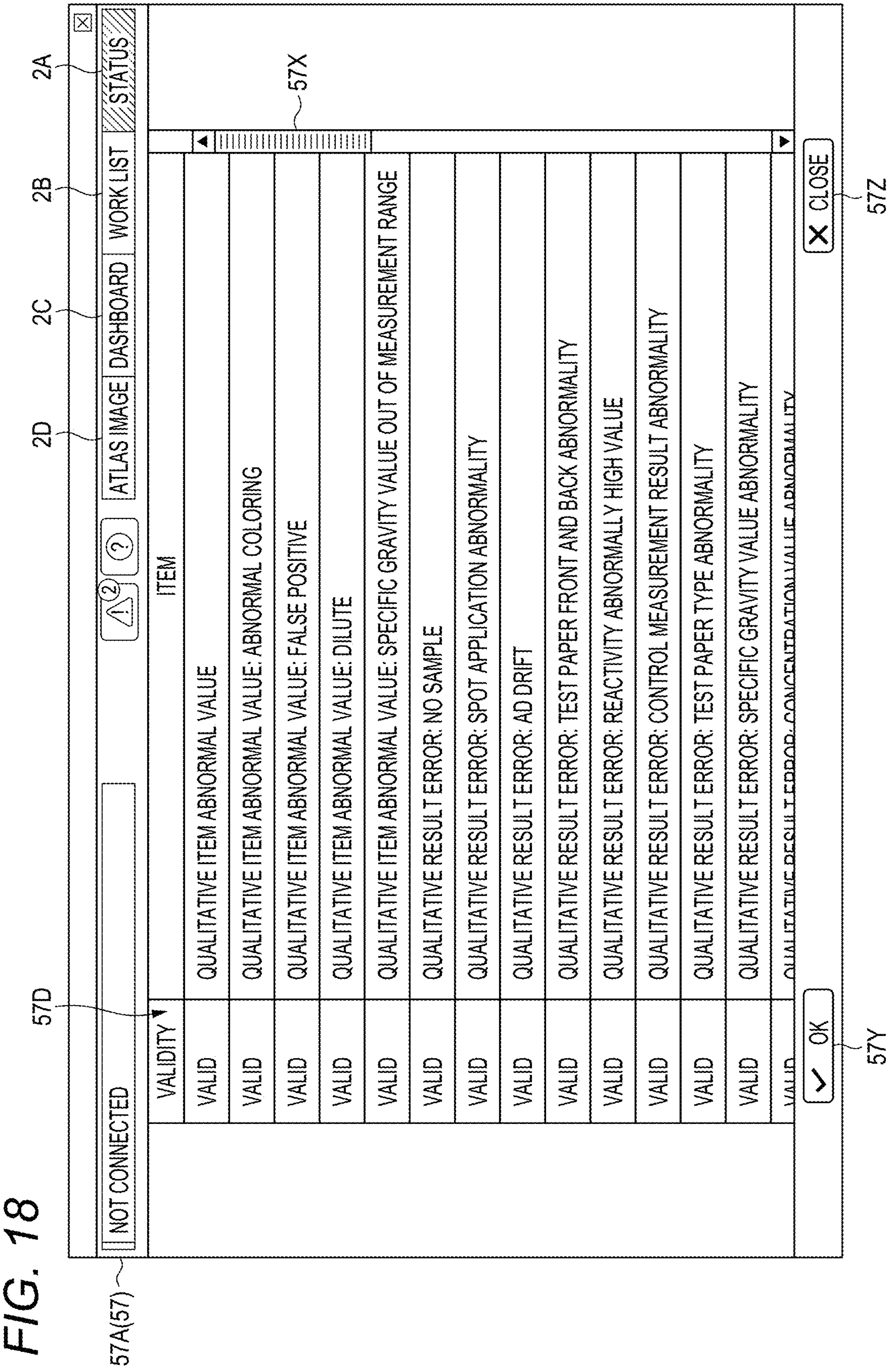
FIG. 18 is a diagram illustrating an example of a flag condition setting screen.

FIG. 18 is a diagram illustrating an example of a flag condition setting screen 57A that is the review condition setting screen 57 for the flag. On the flag condition setting screen 57A, for example, a list of error items that can occur in the urine qualitative analysis device 30 is displayed. When the list of the error items cannot be entirely displayed on the flag condition setting screen 57A, the user may move a scroll bar 57X in the vertical direction to display the flag condition setting screen 57A in a scrolling manner, and all the error items are displayed on the flag condition setting screen 57A.

The error items are associated with respective validity fields 57D. In the validity field 57D, the user may set an associated error item as “Valid” or “Invalid”. By setting the validity field 57D to “Valid”, a review condition is generated that is satisfied when the corresponding error item occurs. When the validity field 57D is set to “Invalid”, a review condition for the corresponding error item is not generated. In this way, the user can edit the validity field 57D to set the review condition for the automatic transmission determination.

For example, when the validity field 57D in an error item “Qualitative Item Abnormality: Abnormal Coloring” is set to “Valid”, a review condition is generated that is satisfied when the urine qualitative test result of the sample includes a test result that abnormal coloring is present in a material component image 3. That is, flag conditions may be triggered where, for example, a result is measurable but is not reliable. For example, a flag condition may be satisfied where the concentration of the specimen exceeds the range that the device can measure.

When a confirm button 57Y is selected, the control unit 10A can temporarily store the review condition generated in the flag condition setting screen 57A in the RAM 13. When a close button 57Z is selected, the output unit 11F can close the flag condition setting screen 57A and display the automatic review request determination screen 56 on the display unit 16.

When the qualitative analysis device 30 executes the qualitative analysis of a sample in operation S40 of FIG. 6, the control unit 10A acquires error information of the qualitative analysis device 30 linked with the same sample ID as the sample ID acquired in operation S10 from the server 35 that stores error information in which abnormality occurring in the urine qualitative analysis device 30 is recorded. The error information is then linked with the sample ID of the sample. When the acquired error information includes information representing that at least one of the error items for which the validity fields 57D are set to “Valid” in the flag condition setting screen 57A occurs, the control unit 10A determines that the review condition is satisfied.

The output unit 11F may display a list of the error items that may occur in each of the devices of the material component processing system 100 on the review condition setting screen 57. Specifically, the output unit 11F displays a list of the error items that may occur in each of the first processing device 10, the qualitative analysis device 30, the server 35, and the urinary material component analysis device 70 on the flag condition setting screen 57A. Here, based on the setting of the user in the flag condition setting screen 57A, the control unit 10A generates the review condition of the flag for at least one of the first processing device 10, the qualitative analysis device such as the urine qualitative analysis device 30, the server 35, and the material component analysis device such as the urinary material component analysis device 70.

In operation S40 of FIG. 6, the control unit 10A acquires the error information of each of the devices linked with the same sample ID as the sample ID acquired in operation S10 from the server 35 that stores the error information of each of the first processing device 10, the urine qualitative analysis device 30, the server 35, and the urinary material component analysis device 70 that is linked with the sample ID. When the acquired error information includes information representing that at least one of the error items of which the validity fields 57D are set to “Valid” in the flag condition setting screen 57A occurs, the control unit 10A determines that the review condition is satisfied.

When the error item of which the validity field 57D is set to “Valid” on the review condition setting screen 57 occurs, the recalculation of the calculated material component concentration is recommended. Accordingly, when the review condition of at least one of the determination items of the first processing device 10, the urine qualitative analysis device 30, the server 35, and the urinary material component analysis device 70 is satisfied, the control unit 10A transmits the material component images 3 of the sample to the second processing device 20 for review.

It should be understood that the control unit 10A may directly acquire the error information generated from each of the first processing device 10, the urine qualitative analysis device 30, the server 35, the urinary material component analysis device 70, or some combination thereof.

Figure 19:
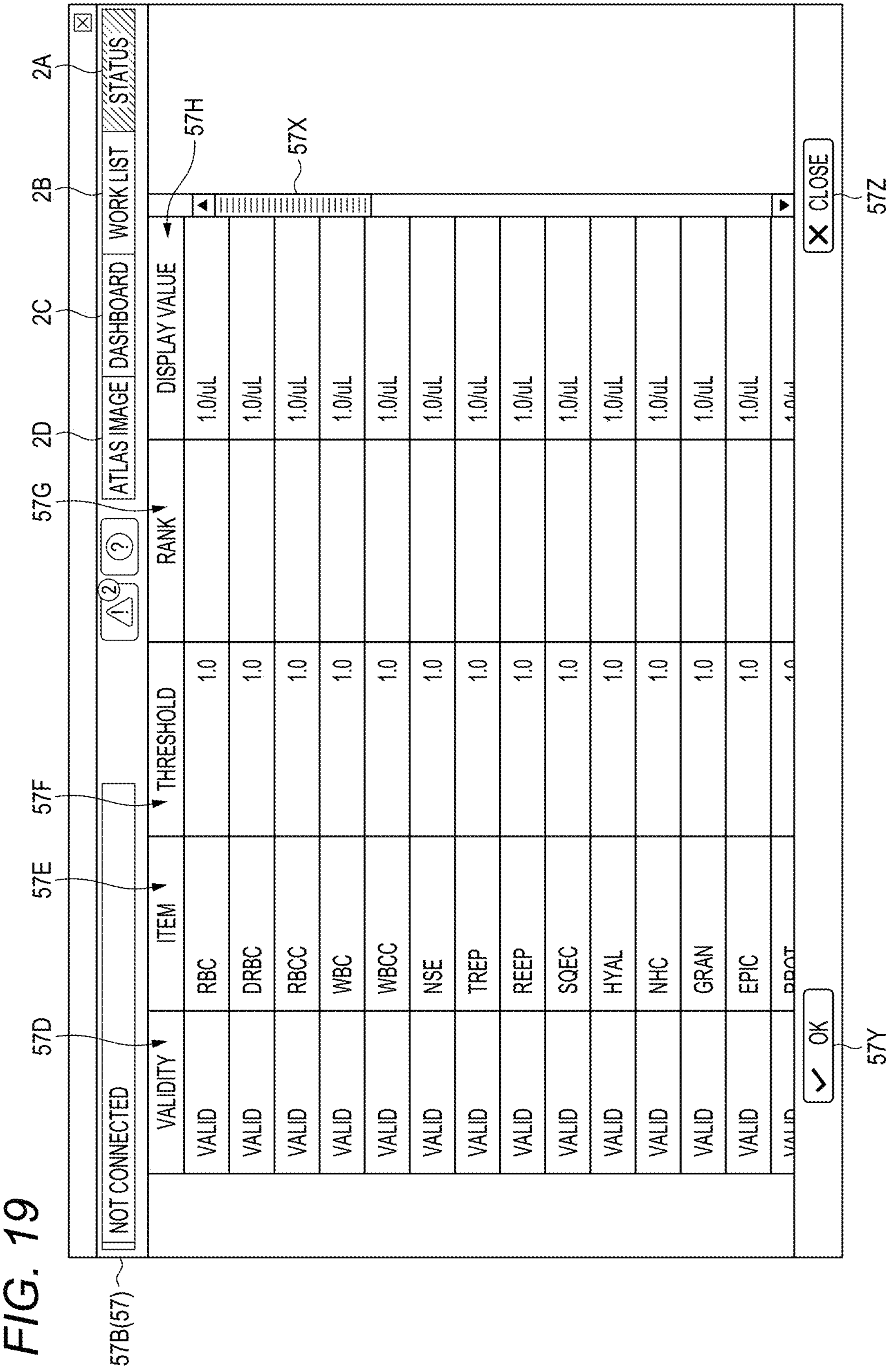
FIG. 19 is a diagram illustrating an example of a material component condition setting screen.

FIG. 19 is a diagram illustrating an example of a material component condition setting screen 57B that is the review condition setting screen 57 for the material component item. In this example, the validity field 57D, an item field 57E, a threshold field 57F, a rank field 57G, and a display value field 57H are displayed on the material component condition setting screen 57B.

In the item field 57E, for example, all types of material components that can be analyzed by the material component analysis device are displayed.

In the threshold field 57F, a threshold of the concentration in the type of material component corresponding to the row direction is set by the user. The threshold field 57F can be edited by the user to set the threshold. The threshold of the concentration may also include comparison information to the threshold. The comparison information to the threshold is information representing a magnitude relationship between the concentration and the threshold, for example representing that the concentration is any one of a "Match with Threshold", the "Threshold or More", the "Threshold or Less", "Less than Threshold", or "More than Threshold". The set threshold may be displayed in the display value field 57H.

In the rank field 57G, section information of the concentration in the type of material component corresponding to the row direction, where used, is set by the user. The rank field 57G can be edited by the user to set the section information. Section information refers to groups when the concentration values are sectioned into a predetermined number of groups, for example, Level 1, Level 2, and Level 3 from the lowest number concentration. The user sets a value in any one of the threshold field 57F or the rank field 57G for the same type of material components.

For example, when the threshold of RBC is set to 1.0 μL or more, and the validity field 57D of RBC is set to "Valid", a review condition is generated that is satisfied when the number concentration of RBC in the sample is 1.0 μL or more. For example, when the rank of RBC is set to Level 1, and the validity field 57D of RBC is set to "Valid", a review condition is generated that is satisfied when the number concentration of RBC in the sample is in the range of Level 1.

When the confirm button 57Y is selected, the control unit 10A temporarily stores the review condition generated in the material component condition setting screen 57B in the RAM 13. When the close button 57Z is selected, the output unit 11F may close the material component condition setting screen 57B and display the automatic review request determination screen 56 on the display unit 16.

When the validity field 57D is set to "Invalid", a review condition based on the concentration in the type of material component is not generated.

In operation S40 of FIG. 6, the control unit 10A refers to the concentration of the type of material component calculated by the calculation unit 11C in operation S30. When the concentration of at least one type of material component of which the validity field 57D is set to "Valid" in the material component condition setting screen 57B satisfies the condition set in the threshold field 57F or the rank field 57G, the control unit 10A determines that the review condition is satisfied.

Figure 20:
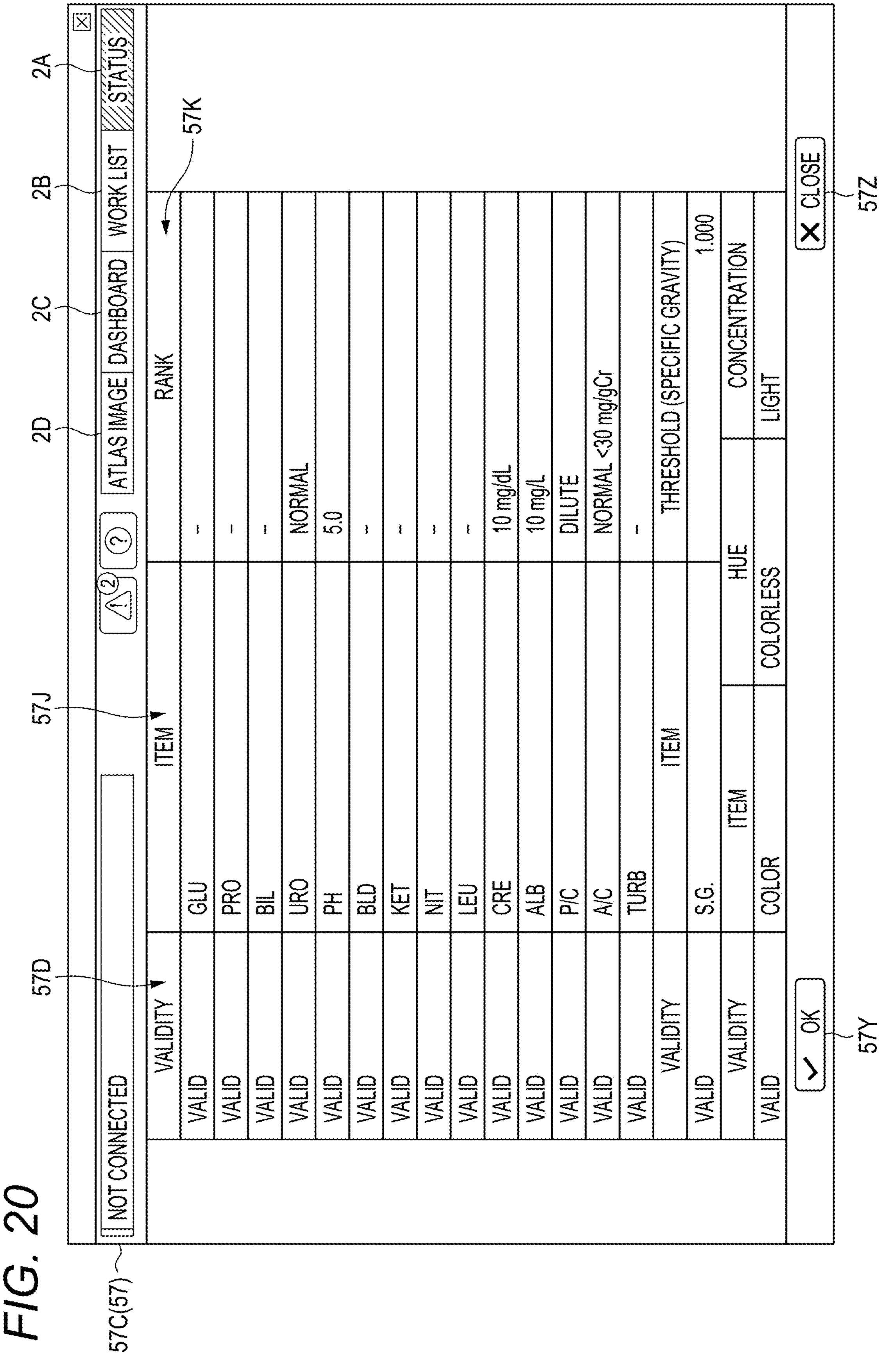
FIG. 20 is a diagram illustrating an example of a qualitative condition setting screen.

FIG. 20 is a diagram illustrating an example of a qualitative condition setting screen 57C that is the review condition setting screen 57 for the qualitative test item. In this example, the validity field 57D, an item field 57J, and a rank field 57K are displayed on the qualitative condition setting screen 57C.

In the item field 57J, for example, all the qualitative items that can be analyzed by the qualitative analysis device are displayed.

In the rank field 57K, a threshold or section information of the qualitative item corresponding to the row direction is set by the user. The rank field 57K can be edited by the user to set the threshold or section information for a corresponding qualitative item.

For example, when the rank of URO is set to "NORMAL", and the validity field 57D of URO is set to "Valid", a review condition is generated that is satisfied when the value of URO in the sample is in a range associated with "NORMAL". For example, when the threshold of creatinine (CRE) is set to 10 mg/dL or more, and the validity field 57D of CRE is set to "Valid", a review condition is generated that is satisfied when the value of CRE in the sample is 1.0 mg/dL or more.

On the qualitative condition setting screen 57C, the name of the rank field 57K corresponding to the type of qualitative item may be replaced with a name such as "hue" or "concentration" with which the setting content can be intuitively grasped by the user.

When the confirm button 57Y is selected, the control unit 10A may temporarily store the review condition generated in the qualitative condition setting screen 57C in the RAM 13. When the close button 57Z is selected, the output unit 11F can close the qualitative condition setting screen 57C and display the automatic review request determination screen 56 on the display unit 16.

When the validity field 57D is set to "Invalid", a review condition based on the value of a corresponding qualitative item is not generated.

In operation S40 of FIG. 6, the control unit 10A refers to the qualitative test result linked with the same sample ID as the sample ID acquired in operation S10 among the sample ID and the urine qualitative test result linked with the sample ID that are stored in the server 35. When the value of at least one qualitative item of which the validity field 57D is set to "Valid" in the qualitative condition setting screen 57C satisfies the condition set in the rank field 57K, the control unit 10A determines that the review condition is satisfied.

As such, when the determination items satisfy the review conditions received by the acceptance unit 11G through the flag condition setting screen 57A, the material component condition setting screen 57B, the qualitative condition setting screen 57C, or some combination thereof, the control unit 10A transmits the material component images 3 of the sample to the second processing device 20 and optionally transmits a review request to the second processing device 20. Receipt of the material component images 3 may optionally trigger a review.

In operation S40 of FIG. 6, the control unit 10A may advance to operation S170 when at least one determination item satisfies the review condition. However, the control unit 10A may proceed to operation S170 when all of a plurality of determination items satisfy the respectively review conditions. For example, the control unit 10A may proceed to operation S170 when the concentrations of RBC and deformed red blood cells (DRBC) in the material component condition setting screen 57B illustrated in FIG. 19 both satisfy the review conditions. The combination of the plurality of determination items may be any one of a combination of types in the same determination item or a combination of different types in different determination items.

When a review condition is generated for the determination item in any of the flag condition setting screen 57A, the material component condition setting screen 57B, or the qualitative condition setting screen 57C, but the determination item is set to "Not Determine" by a respective pulldown list 56A, 56B, or 56C of the automatic review request determination screen 56, the control unit 10A does not transmit the review request to the second processing device 20 even if the determination item satisfies the review condition. That is, the process advances to operation S50 without executing operation S180. Accordingly, the user can invalidate the determination target of the review condition for each of the types of determination items simply by setting a pulldown list 56A, 56B, or 56C without setting the validity field 57D that has been set to "Valid" back to "Invalid".

In the present embodiment, whether the determination item satisfies the review condition is determined in operation S40, and whether the automatic transmission setting to the second processing device 20 is made for the determination item satisfying the review condition is determined in operation S170. In another embodiment, whether the determination item for which the automatic transmission setting to the second processing device 20 is made is present may be determined after operation S30, and whether the review condition is satisfied may be determined only for the determination item for which the automatic transmission setting is made. Then, when the review condition is satisfied, the process advances to operation S180. In this modification, it is only necessary to check the review condition of the determination item for which the automatic transmission setting is made. Therefore, the necessity of automatic transmission can be efficiently determined.

In each of the embodiments, the processor refers to a processor in a broad sense, and includes a general-purpose processor, for example, central processing unit (CPU), or a dedicated processor, for example, a graphics processing unit (GPU), an application specific integrated circuit (ASIC), a field programmable gate array (FPGA), or a programmable logic device or programmable logic controller (PLC).

In each of the embodiments, operation of the processor may be implemented by one processor or may be implemented in cooperation with a plurality of processors disposed at positions that are physically separated from each other. The order of operations of the processor(s) is not limited to only the order described in each of the embodiments and may be appropriately changed.

Hereinabove, the first processing device 10 according to an embodiment has been described. The embodiment may be in the form of a program for causing a computer to execute the function of each of the units in the first processing device 10. The embodiment may be in the form of a computer-readable non-transitory storage medium storing the program.

The configuration of the first processing device 10 described above is by example and may be changed depending on the material component processing device without departing from the scope of the present disclosure. The display of the material component images 3 is not limited to the above-described embodiment, and the material component images 3 may be displayed horizontally side by side or elsewise. The display position of each of the buttons can be appropriately changed.

The flow of the processes of the programs described in the above-described embodiments are by example only. An unnecessary operation may be deleted, a new operation may be added, or the processing order may be changed while not departing from the scope of the present disclosure.

In the above-described embodiments, the processes are implemented as a software configuration by a computer executing the program. However, the present disclosure is not limited thereto. The embodiments may be implemented, for example, by a hardware configuration or by a combination of a hardware configuration and a software configuration.

The teachings herein provide an effect that a user can be supported in the determination of whether reclassification of a material component images is necessary to improve the material component concentrations determined from a sample.

In some implementations, whether the reclassification of the material component images is necessary can be determined using at least one of qualitative test result of the sample or error information in the qualitative analysis device.

In some implementations, the user can set the review condition depending on statuses.

In some implementations, the transmission of the material component images of the sample to a remote, second processing device without permission of the user can be prevented.

In some implementations, how the classification of the material component images is executed by the first processing device can be checked in the second processing device.

In some implementations, the determination of whether reclassification of the material component images of each of the material components in urine is necessary can be supported.

As is clear from the above description, a material component image may be reclassified when there is a doubt about its initial classification by the classification unit such that the concentrations of the material components in the sample are not accurate. However, even if all material component images are correctly classified, some or all may be reclassified into more detailed groupings that possible using the classification unit. That is, there may be limitations in the number of classification types/groups for the material components in the first classification unit such that the second classification unit can provide support for those types/groups. For example, in the description above, an example is provided where a material component is a red blood cell (RBC) in the first classification unit. The second classification unit can reclassify the red blood cells in more detail (e.g., Isomorphic RBC or Dysmorphic RBC).

As is also clear from the above description, all extracted and classified/reclassified images are needed to calculate a concentration. Therefore, the control unit can send all images to the second, remote processing device, which can reclassify and calculate the concentration values in some implementations to, for example, confirm the accuracy of the first processing device. This can occur instead of sending only some images for reclassification based on the various conditions, including the determination items, such as the flags shown by example in FIG. 18, the material component items shown by example in FIG. 19, and the qualitative test items shown by example in FIG. 20. In another example, to reclassify a particular classification, like the RBC example above, those classified as the particular classification may be sent alone, or optionally with any images not classified or otherwise identified by the conditions.

It is worth noting that it is not necessary to initially calculate the concentration values at the first processing device (i.e., before sending images for reclassification). Instead, the concentration values can be calculated for the first time at the first processing device after receiving the reclassifications from the second processing device such that the initial groupings have changed. This is particularly useful when reclassifying is done in response to a qualitative test item as the condition or criteria for reclassification.

It is further worth noting that the use of the term reclassification herein does not mean that the classification of a material component image must change from its initial classification. The reclassification may confirm the initial classification for any particular material component image. In some implementations, none of the initial classifications may change due to the reclassification.

The above-described embodiments, implementations, and aspects have been described to allow easy understanding of the present invention and do not limit the present invention. On the contrary, the invention is intended to cover various modifications and equivalent arrangements included within the scope of the appended claims, which scope is to be accorded the broadest interpretation to encompass all such modifications and equivalent structure as is permitted under the law.

What is claimed is:

1. An apparatus for determining material component concentrations in a sample, comprising:
an imaging device for imaging a sample including material components to produce sample images;
an acquisition unit configured to acquire material component images of respective material components from at least some of the sample images;
a classification unit configured to classify the material component images into respective groups corresponding to a respective type of material component of the material components shown within a material component image, wherein a concentration of the material component in the sample is based on a cardinality of the material component images classified into a group of the groups corresponding to the material component;
a transmission unit configured to transmit at least one material component image of the material component images as classified to a remote processing device through a network, the remote processing device configured to reclassify the at least one material component image and return reclassification information for the at least one material component image; and
an output unit configured to output at least one of a first status, a second status, or a third status for a respective material component image of the at least one material component image, the first status representing a status after the classification unit classifies the material component image and representing a status of waiting for an instruction to transmit the material component image to the remote processing device, the second status representing a status of waiting to receive the reclassification information from the remote processing device, and the third status representing a status where the reclassification information for the material component image is received from the remote processing device.

2. The apparatus of claim 1, further comprising:
a calculation unit configured to calculate a concentration of at least one material component of the material components in the sample using the reclassification information.

3. The apparatus of claim 2, wherein an updated model for the classification unit is trained using results from the classification unit and the reclassification information.

4. The apparatus of claim 1, further comprising:
a reception unit configured to receive the reclassification information from the remote processing device.

5. The apparatus of claim 1, wherein the third status includes a fourth status representing a status where the reclassification information is received from the remote processing device and the reclassification information does not include a recommendation to perform a predetermined test, and a fifth status representing a status where the reclassification information is received from the remote processing device and the reclassification information includes a recommendation to perform the predetermined test.

6. The apparatus of claim 5, wherein the predetermined test comprises microscopy.

7. The apparatus of claim 1, wherein the output unit is a display unit.

8. The apparatus of claim 7, wherein the display unit displays each of the first status, the second status, and the third status for multiple samples.

9. The apparatus of claim 1, wherein the sample is urine.

10. A system for determining material component concentrations in a sample, comprising:
the apparatus of claim 1 as a first processing device; and
the remote processing device as a second processing device connected to the first processing device through the network, wherein the second processing device includes:
a reclassification unit configured to reclassify a material component image among the at least some of the material component images received from the first processing device into a group corresponding to a type of a material component different from that determined by the classification unit; and
a return unit configured to return a reclassification result of the material component image reclassified by the reclassification unit to the first processing device.

11. The system of claim 10, wherein:
the reclassification unit comprises a trained machine-learning model.

12. A method for determining material component concentrations in a sample, comprising:
imaging, using an imaging device, a sample including material components to produce sample images;
acquiring, using an acquisition unit, material component images of respective material components from at least some of the sample images;
classifying, using a classification unit, the material component images into respective groups corresponding to a respective type of material component of the material components shown within a material component image, wherein a concentration of the material component in the sample is based on a cardinality of the material component images classified into a group of the groups corresponding to the material component;
transmitting, using a transmission unit, at least one material component image of the material component images as classified to a remote processing device through a network, the remote processing device configured to reclassify the at least one material component image and return reclassification information for the at least one material component image; and
outputting, using an output unit, at least one of a first status, a second status, or a third status for a respective material component image of the at least one material component image, the first status representing a status after the classification unit classifies the material component image and representing a status of waiting for an instruction to transmit the material component image to the remote processing device, the second status representing a status of waiting to receive the reclassification information from the remote processing device, and the third status representing a status where the reclassification information for the material component image is received from the remote processing device.

13. The method of claim 12, wherein transmitting the at least one material component image comprises transmitting all of the material component images as classified through the network to the remote processing device.

14. The method of claim 12, further comprising:

calculating, using a calculation unit, a concentration of at least one material component of the material components in the sample using the reclassification information.

15. The method of claim 14, comprising:

calculating, using the calculation unit, a respective concentration of the material components in the sample using the groups before receiving the reclassification information.

16. The method of claim 12, comprising:

calculating, using a calculation unit, a respective concentration of the material components in the sample using the groups before receiving the reclassification information.

17. A non-transitory storage medium storing instructions that cause a processor to execute a process for determining material component concentrations in a sample, the process comprising:

imaging a sample including material components to produce sample images;

acquiring material component images of respective material components from at least some of the sample images;

classifying the material component images into respective groups corresponding to a respective type of material component of the material components shown within a material component image, wherein a concentration of the material component in the sample is based on a cardinality of the material component images classified into a group of the groups corresponding to the material component;

transmitting at least one material component image of the material component images as classified to a remote processing device through a network, the remote processing device configured to reclassify the at least one material component image and return reclassification information for the at least one material component image; and outputting at least one of a first status, a second status, or a third status for a respective material component image of the at least one material component image, the first status representing a status after the material component image is classified and representing a status of waiting for an instruction to transmit the material component image to the remote processing device, the second status representing a status of waiting to receive the reclassification information from the remote processing device, and the third status representing a status where the reclassification information for the material component image is received from the remote processing device.

* * * * *